US010744149B2

(12) United States Patent
Ruderman Chen et al.

(10) Patent No.: US 10,744,149 B2
(45) Date of Patent: *Aug. 18, 2020

(54) MAINTENANCE OF PLATELET INHIBITION DURING ANTIPLATELET THERAPY

(71) Applicant: Chiesi Farmaceutici S.p.A., Parma (IT)

(72) Inventors: Lisa Ruderman Chen, Rye, NY (US); Simona Skerjanec, Basel (CH); Dawn Bell, Morristown, NJ (US); Jayne Prats, Carlisle, MA (US); Meredith Todd, Hoboken, NJ (US)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/356,798

(22) Filed: Mar. 18, 2019

(65) Prior Publication Data

US 2019/0321385 A1  Oct. 24, 2019

Related U.S. Application Data

(63) Continuation of application No. 14/195,798, filed on Mar. 3, 2014, now Pat. No. 10,231,987, which is a continuation of application No. 13/209,271, filed on Aug. 12, 2011, now abandoned, which is a continuation-in-part of application No. 12/990,332, filed as application No. PCT/US2009/043820 on May 13, 2009, now Pat. No. 8,871,736.

(60) Provisional application No. 61/127,414, filed on May 13, 2008.

(51) Int. Cl.
*A61K 31/7076* (2006.01)
*A61K 31/4365* (2006.01)
*A61K 31/00* (2006.01)

(52) U.S. Cl.
CPC .......... *A61K 31/7076* (2013.01); *A61K 31/00* (2013.01); *A61K 31/4365* (2013.01)

(58) Field of Classification Search
CPC ............ A61K 31/4365; A61K 31/7076; A61K 31/00; A61K 2300/00
See application file for complete search history.

(56) References Cited

U.S. PATENT DOCUMENTS

| 4,529,596 | A | | 7/1985 | Aubert et al. |
| 5,256,559 | A | | 10/1993 | Maraganore et al. |
| 5,288,726 | A | | 2/1994 | Koike et al. |
| 5,721,219 | A | * | 2/1998 | Ingall ..................... C07H 19/20 514/47 |
| 5,955,447 | A | * | 9/1999 | Ingall ..................... C07H 19/20 514/47 |
| 6,114,313 | A | * | 9/2000 | Bland ................... A61K 9/0019 514/47 |
| 6,130,208 | A | * | 10/2000 | Broadhead ............. C07H 17/08 514/47 |
| 6,693,115 | B2 | | 2/2004 | Asai et al. |
| 6,861,424 | B2 | | 3/2005 | Bryant et al. |
| 8,680,052 | B1 | * | 3/2014 | Arculus-Meanwell ....... A61K 9/0019 514/14.7 |
| 8,716,261 | B2 | * | 5/2014 | Ruderman Chen .... A61K 45/06 514/234.5 |
| 8,759,316 | B2 | * | 6/2014 | Ruderman Chen ......... A61K 31/7076 514/327 |
| 8,871,736 | B2 | * | 10/2014 | Chen .................... A61K 31/00 514/47 |
| 9,320,754 | B2 | * | 4/2016 | Ruderman Chen .... A61K 45/06 |
| 9,427,448 | B2 | * | 8/2016 | Arculus-Meanwell ....... A61K 9/0019 |
| 9,925,265 | B2 | * | 3/2018 | Arculus-Meanwell ....... A61K 9/0019 |
| 10,231,987 | B2 | * | 3/2019 | Ruderman Chen ......... A61K 31/4365 |
| 2006/0121086 | A1 | | 6/2006 | Boyer |
| 2006/0270607 | A1 | | 6/2006 | Dixon |
| 2007/0082740 | A1 | | 4/2007 | Porter |
| 2007/0254324 | A1 | | 11/2007 | Rechner |
| 2009/0247465 | A1 | | 10/2009 | Baldo |
| 2011/0081657 | A1 | | 4/2011 | Coller et al. |
| 2011/0112030 | A1 | | 5/2011 | Arculus-Meanwell et al. |
| 2012/0141468 | A1 | | 6/2012 | Chen et al. |
| 2013/0190265 | A1 | | 7/2013 | Arculus-Meanwell et al. |
| 2013/0303477 | A1 | | 11/2013 | Ruderman Chen et al. |
| 2013/0303478 | A1 | | 11/2013 | Ruderman Chen et al. |

FOREIGN PATENT DOCUMENTS

| CA | 2724470 A1 | 11/2009 |
| CN | 103860459 A | 6/2014 |
| WO | 2005097814 A2 | 10/2005 |
| WO | 2006199507 A2 | 11/2006 |

(Continued)

OTHER PUBLICATIONS

Vasiljev KS, Uri A, Laitinen JT, 2-Alkylthio-substituted platelet P2Y12 receptor antagonists reveal pharmacological identity between the rat brain Gi-linked ADP receptors and P2Y12, Neuropharmacol, 2003, pp. 145-154, vol. 45, No. 1.

Voisin et al., "Are P2Y12 reaction unit {Pru) and % inhibition index equivalent for the expression of P2Y12 inhibition by the VerifyNoVv® assay? Role of haematocrit and haemoglobin levels," Thromb Haemost 2011; 106: 227-229.

Wallentin et al., Ticagrelor versus Clopidogrel in Patients with Acute Coronary Syndromes, The New England Journal of Medicine, 2009, vol. 361, No. 11, 1045-1057.

(Continued)

*Primary Examiner* — Lawrence E Crane
(74) *Attorney, Agent, or Firm* — Vorys, Sater, Seymour and Pease LLP; Maryellen Feehery Hank (57) ABSTRACT

A method for reducing or maintaining platelet inhibition in a patient by administering cangrelor prior to an invasive procedure is described. The method of this invention can be used for patients in need of antiplatelet therapy or at risk of thrombosis. The method can further be used in patients who were previously treated with long-acting platelet inhibitors without increasing the risk of excessive bleeding.

47 Claims, 3 Drawing Sheets

(56) References Cited

FOREIGN PATENT DOCUMENTS

| WO | 2007024472 A2 | 3/2007 |
|---|---|---|
| WO | 2011134478 A2 | 11/2011 |

OTHER PUBLICATIONS

Wang K, Zhou X, Zhou Z, et al., Blockade of the ADP P2T receptor sustains coronary artery recanalization and improves the myocardium tissue perfusion in the canine thrombosis model, Circulation, 2001, p. 96, vol. 104 (17 Suppl).
Wang K, Zhou X, Zhou Z, et al., Blockade of the platelet P2Y12 receptor by AR-C69931MX sustains coronary artery recanalization and improves the myocardial tissue perfusion in a canine thrombosis model, Arterioscler Thromb Vasc Biol, 2003, pp. 357-362, vol. 23, No. 1.
Wang K, Zhou X, Zhou Z, et al., Sustained coronary artery recanalization with adjunctive infusion of a novel P2T-receptor antagonist AR-C69931 in a canine model, Jacc, 2000, pp. 281A-282A, vol. 35(2 Suppl).
Weaver WD, Becker R, Harrington R, et al., Safety and efficacy of a novel direct P2T receptor antagonist, AR 6991MX, in patients undergoing percutaneous coronary intervention, Eur Heart J, 2000, p. 382, vol. 21 (Suppl).
Weaver Wd, Harrington RA, Grines CL, et al., Intravensous AR C69931MX, a novel P2T platelet receptor antagonist, in patients undergoing percutaneous coronary interventions preliminary results from a placebo or active controlled trial, Jacc, 2000, pp. 36A-37A, vol. 35 (2SupplA).
White HD, Chew DP Dauerman HL, et al., Reduced immediate ischemic events with cangrelor in PCI. A pooled analysis of the Champion trials using the universal definition of myocardial infarction, Am Heart J, 2012, pp. 182-190. e4, vol. 163.
Wiviott SD, De Lemos JA, Antiplatelet agents make a comeback in ST-elevation myocardial infarction, Am Heart J, 2007, pp. 603-606, vol. 154.
Wiviott SD, Michelson AD, Berger PB, et al., Therapeutic goals for effective platelet inhibition: a consensus document, Rev Cardiocasc Med, 2006, pp. 214-225, vol. 7.
Xiang, B., et al., The P2Y12 Antagonists, 2MeSAMP and Cangrelor, Inhibit Platelet Activation through P2Y12/i-Dependent Mechanism, PLOS One, 2012, pp. 1-10, vol. 7, Issue 12.
Kumar et al., Fundamentals and Applications of Lyophilization. 2(4) J. Adv. Pharm. Res. 157 (2011).
ClinicalTrials.Gov, "Cangrelor Versus Standard Therapy to Achieve Optimal Management of Platelet Inhibition." NCT00385 I 38 (Aug. 29, 2008).
Brilinta (ticagrelor) Prescribing Information (Jul. 2011).
Freeze Drying/ Lyophilization of Pharmaceutical and Biological Products, 2010, Edited by L. Rey etc. (Drugs and the Pharmaceutical Sciences, vol. 206) pp. 246, 256-260, 396, 400, 406-411, 451.
Fox et al. Circualtion. 2004, 110, 1201-08.
Fox SC, May JA, Johnson A, et al., Effects on platelet function of an EP3 receptor antagonist used alone and in combination with P2Y12 antagonist both in-vitro and ex-vivo in human volunteers, Plateles, 2013, pp. 392-400, vol. 24, No. 5.
Fox SC, May JA, Johnson A, et al., Effects on platelet function of an EP3 receptor antagonist used alone and in combination with P2Y12 antagonist both in-vitro and ex-vivo in human volunteers, Platelets, 2013, pp. 392-400, vol. 24, No. 5.
Fugate, S.E. et al. Cangrelor for Treatment of Coronary Thrombosis, The Annals of Pharmacotherapy, 2006, pp. 925-930, vol. 40.
Geisler T. Gawaz M, Steinhubl SR, et al., Current strategies in antiplatelet therapy—Does identification of risk and adjustment of therapy contribute to more effective, personalized medicine in cardiovascular disease?, Pharmacol Ther, 2010, pp. 95-107, vol. 127.
Gitt AK, Betriu A., Antiplatelet therapy in acute coronary syndromes, Eur Heart J, 2008, pp. A4-A12, 10 Supp. A.
Greenbaum AB, Grines CL, Bittl JA, et al., Initial experience with an intravenous P2YI2 platelet receptor antagonist in patients undergoing percutaneous coronary intervention: Results from a 2-part, phase II, multicenter, randomized, placebo- and active-controlled trial, Am Heart J, 2006, pp. 689.el-689.elO.
Greenbaum AB, Ohman EM, Gibson MS, et al., Intravenous adenosine diphosphate P2T platelet receptor antagonsim as an adjunct to fibrinolysis for acute myocardial infarction, JACC, 2002, pp., vol. 39, Issue 5, Supp. A.
Greenbaum, A.B., et al., Preliminary experience with intravenous P2Y.sub.12 platelet receptor inhibitions as an adjunct to reduced-dose alteplase during acute myocardial infarction: Results of the Safety, Tolerability and Effect on Patency in acute Myocardial Infarction (STEP-AMI) angiographic trial, 2007, pp. 702-709, vol. 154, No. 4.
Gurbel et al., "Oral Dosing of PRT060128, a Novel Direct-acting, Reversible P2Y12 Antagonist Overcomes High Platelet Reactivity in Patients Non-responsive to Clopidogrel Therapy," Circulation. 2008;118:S_972, abstract.
Gurbel et al., "Peri-operative platelet function testing: The potential for reducing ischaemic and bleeding risks," Thromb Haemost 2011; 106: 248-252.
Hall R, et al., Antiplatelet drugs: a review of their pharmacology and management in the perioperative period, Anesthesia & Analgesia, 2011, pp. 292-318, vol. 112, No. 2.
Harrington RA, Stone GW, McNulty S, et al., Platelet inhibition with cangrelor in patients undergoing PCI, N Engl J Med, 2009, pp. 2318-2319, vol. 361.
Highlights of prescribing information for Brilinta, Sep. 2015.
Ho et al. Incidence of death and acute myocardial infarction associated with stopping dopidogrel after acute coronary syndrome. JAMA. Feb. 6, 2008; 299(5):532-9).
Ho PM et al. Jama, Feb. 6, 2008, 299(5):532-9.
Huang J, Driscoll EM, Gonzales ML, Prevention of arterial thrombosis by intravenously administered platelet P2T receptor antagonist AR-C66931MX in a canine model, J Pharmacol Exp Ther, 2000, pp. 492-499, vol. 295, No. 2.
Humphries RG, Pharmacology of AR-C69931MX and related compounds: from pharmacological tools to clinical trials, Haematologica, 2000, pp. 66-72, 85(the Platelet ADP Receptors Supp).
Ingall AH, Dixon J, Bailey A, et al., Antagonists of the platelet P2T receptor: a novel approach at antithrombotic therapy, J Med Chem, 1999, pp. 213-220, vol. 42.
Ingall AH, P2T receptor antagonists: novel inhibitors of platelet aggregation, Arch Pharm 1999, pp. 11-12, Supp. 1.
International Search Report and Written Opinion by the International Searching Authority, dated Feb. 10, 2015, in the PCT Application No. PCT/US2014/059972.
International Search Report and Written Opinion by the International Searching Authority, dated Jan. 3, 2014, in the PCT Application No. PCT/US2013/048735.
International Search Report and Written Opinion by the International Searching Authority, dated Jun. 11, 2009, in the PCT Application No. PCT/US09/42681.
International Search Report and Written Opinion by the International Searching Authority, dated Jun. 30, 2009, in the PCT Application No. PCT/US09/43820.
Iyu D, Glenn JR, White AE, et al., Adenosine-derived from ADP can contribute to inhibition of platelet aggregation in the presence of a P2Y12 antagonist, Arterioscler Thromb Vasc Biol, 2011, pp. 416-422, vol. 31.
Jacobsson F, Dellborg M, Swahn E, et al., JACC, 2000, p. 343, vol. 35, Issue 2, Supp. A.
Jacobsson F, Swahn E, Wallentin L, et al., Safety profile and tolerability of intravenous AR C69931MX, a new antiplatelet drug in unstable angina pectoris and non Q wave myocardial infarction, Clin Ther, 2002, pp. 752-765, vol. 24, No. 5.
Jarvis GE, Nassim MA, Humphries RG, et al., Superior inhibition of ADP induced human platelet aggregation by AR C69931MX than clopidogrel. Drug Dev Res, 2000, p. 90. vol. 50, No. 1.

(56) References Cited

OTHER PUBLICATIONS

Jarvis GE, Nassim MA, Humphries RG, et al., The P2T antagonists AR C69931MX is a more effective inhibitor of ADP induced platelet aggregation than clopidogrel, Blood. 1999, p. 194 (10 Supp. pt. 1):22a.
Judge HM, Buckland RJ, Holgate CE, et al. Glycoprotein llb/llla and P2Y12 receptor antagonists yield additive inhibition of platelet aggregation, granule secretion, soluble CD40L release and procoagulant responses, Platelets, 2005, pp. 398-407, vol. 16, No. 7.
Kandzari DE, Evolving antithrombotic treatment strategies for acute ST-elevation myocardial infarction, Rev Cardiovasc Med, 2006, pp. S29-S37, vol. 7, Supp. 4.
Krajewski, S., et al., Short-acting P2Y12 blockade to reduce platelet dysfunction and coagulopathy during experimental extracorporeal circulation and hypothermia, BJA, 2012, pp. 912-921, vol. 108, No. 6.
Kuijpers MJ, Nieuwenhuys CM, Feijge MA, et al., Regulation of tissue factor-induced coagulation and platelet aggregation in flowing whole blood, Thromb Haemost, 2005; 93, pp. 97-105.
Kunapuli SP, Ding Z, Dorsam RT, et al., ADP receptors target for developing antithrombotic agents, Curr Pharm Des, 2003, vol. 9, pp. 2303-2316.
Leon C, Alex M. Klocke A. et al., Platelet ADP receptors contribute to the initiation of intravascular coagulation, Blood 2004, pp. 594 600, vol. 103, No. 2.
Leonardi S, et al., Pre-treatment with thienopyridines reduces the amount of myonecrosis in acute coronary syndrome patients invasively managed: insights from the Champion trials, Circulation, 2010, p. AI4813, vol. 122, No. 21, Suppl. S, Nov. 2010 (Nov. 2011).
Leonardi S, Stebbins A, Lopes RD, et al., Maintenance therapy with thienopyridines may reduce enzymatic infarct size in patients with acute coronary syndrome undergoing PCI: Insights from the Champion PCI trial, AHA Chicago, IL, 2010.
Leonardi S, Truffa AA, Neely LM, et al., A novel approach to systematically implement the universal definition of myocardial infarction: insights from the Champion Platform trial, Heart, 2013, pp. 1282-1287, vol. 99.
Lepantalo et al., "Antiplatelet effect of clopidogrel in patients with aspirin therapy undergoing percutaneous coronary interventions-limited inhibition of the P2Y12 receptor," Thromb Res. Jun. 2009;124(2):193-8.
Iyu D, Glenn JR, White, AE, et al., Mode of action of P2Y12 antagonists as inhibitors of platelet function, Thromb Haemost, 2011, pp. 96-105, vol. 105.
Mazzucato M, Cozzi MR, Pradella P, et al., Crucial role of the ADP receptor P2Y1 in platelet adhesion and signaling under high flow, Blood, 2002, p. 100, 11.
Michelson AD, P2Y12 Antagonism. Promises and challenges, Arterioscler Thromb Vasc Biol. 2008; pp. S33-S38.
Murugappan S, Kunapulis, The role of ADP receptors in platelet function, Front Biosci, 2006, pp. 1977-1986, vol. 11.
Nassim MA, Sanderson JB, Clarke C, et al., Investigation of the novel P2T receptor antagonist AR C69931MX on ex vivo adenosine diphosphate induced platelet aggregation and bleeding time in healthy volunteers, Jacc, 1999, p. 33, vol. 33 (Supp A).
Niitsu Y, Jakubowksi JA, Sugidachi A, et al., Pharmacology of CS-747 (Prasugrel, LY640315), a novel, potent antiplatelet agent in vivo P2Y12 receptor antagonist activity, Semin Thromb Hemost, 2005, pp. 184-194, vol. 31, No. 2.
Norgard Nogard NB, Abu-Fadel, M, Future prospects in antiplatelet therapy: A review of potential P2Y12 and thrombin receptor antagonists. Recent Patents Cardiovasc Drug Discovery, 2008, pp. 194-200, vol. 3.
Porter et al. (eds.), A portion of "Coronary Artery Disease," Chapter 210 in the Merck Manual of Diagnosis and Therapy, 19th Edition, Merck & Co., Inc., Rahway, N J, 2011, only title pages and text pp. 2087-2110 supplied.

Beers et al. (eds.), "Coronary Artery Disease," Chapter 73 in the Merck Manual of Diagnosis and Therapy, 18th Edition, Merck & Co., Inc., Rahway, N J, Jan. 2006, only title pages and text pp. 626-652 supplied.
Abbracchio MP, et al., International union of pharmacology L VIII: update on the P2Y G protein-coupled nucleotide receptors: from molecular mechanisms and pathophysiology to therapy, Pharmacol Rev, 2006, pp. 281-321, vol. 58, No. 3.
Accumetric, LLC, "VerifyNow User System User Manual," 2009.
Ahrens, I., et al., Novel antiplatelet therapies following percutaneous coronary interventions, Current Opinion in Investigational Drugs, 2009, pp. 902-911, vol. 10, No. 9.
Akers, W.S., et al., Pharmacokinetics and Pharmacodynamics of a Bolus and Infusion of Cangrelor: A Direct Parenteral P2Y12 Receptor Antagonist, the J Clin. Pharmacol, 2009, pp. 26-35, vol. 50.
Aleil B, et al., Flow cytometric analysis of intraplatelet VASP phosphorylation for the detection of clopidogrel resistance in patients with ischemic cardiovascular diseases, J Thromb Haemost, 2005, pp. 85-92.
Angiolillo DJ, ADP Receptor Antagonism. What's in the Pipeline?, Am J Cardiovasc Drugs, 2007, pp. 423-432. vol. 7 No. 6.
Angiolillo DJ, et al., Pharmacology of emerging novel platelet inhibitors, Am Heart J, 2008, pp. S10-S15, vol. 156, No. 2, Supp. 1.
Angiolillo DJ, et al., Randomized Comparison of a High Clopidogrel Maintenance Dose in Patients with Diabetes Mellitus and Coronary Artery Disease, Circulation, 2007, 708-716, 115.
Angiolillo, D.J., et al., Bridging Antiplatelet Therapy With Cangrelor in Patients Undergoing Cardiac Surgery: A Randomized Controlled Trial, Original Contribution, JAMA, 2012, pp. 265-274, vol. 307, No. 3.
Angiolillo, D.J., et al., Clinical overview of promising nonthienopyridine antiplatelet agents, AHJ, 2008, pp. S23-S28, vol. 156, No. 2, Supp. I.
Angiolillo, D.J., et al., Pharmacodynamic effects of cangrelor and clopidogrel: the platelet function substudy from the cangrelor versus standard therapy to achieve optimal management of platelet inhibition (Champion) trials, J.Thromb Thr., 2012, pp. 44-55, vol. 34.
Anonymous: "NCT00767507 on Aug. 8, 2011: Clinicaltrials.gov Archive", Aug. 8, 2011 (Aug. 8, 2011), XP055177258, Retrieved from the Internet: URL https://clinicaltrials.ov/archive/NCT00767507/2011_08_08 [retrieved on Mar. 17, 2015].
Anonymous: "NCT00767507 on Oct. 6, 2008: Clinicaltrials.gov Archive", Oct. 6, 2008 (Oct. 6, 2008), XP055177260, Retrieved from the Internet: URL https://clinicaltrials.ov/archive/NCT00767507/2008_10_06 [retrieved on Mar. 17, 2015].
Barker CM, Price MJ, Antiplatelet therapy in acute coronary syndromes, Curr Cardiol Rep, 2008, pp. 327-333, vol. 10, No. 4.
Bassand, J-P, Unmet needs in antiplatelet therapy, EHJ Supplements, 2008, pp. D3-D11, vol. 10, Supp. D.
Becker RC, Platelet surface physiology and its importance in pharmacotherapy design and development: The adenosine diphosphate receptor antagonists, J Thromb Thrombolysis, 2000 pp. 35-53.
Becker, R.C., et al., Management of Platelet-Directed Pharmacotherapy in Patients With Atherosclerotic Coronary Artery Disease Undergoing Elective Endoscopic Gastrointestinal Procedures, JACC, 2009, pp. 2261-2276, vol. 54, No. 24.
Bellemain-Appaix A. Brieger D, Beygiu F, et al., New P2Y12 inhibitors versus clopidogrel in percutaneous coronary intervention, a Meta-analysis, J Am Coll Cardiol, 2010, pp. 1542-1551, vol. 56.
Berger et al. Clinical implications of percutaneous coronary intervention-clopidogrel in unstable angina to prevent recurrent events (PCI-Cure) study: a US perspective. Circulation. Oct. 22, 2002;106(17):2284-7.
Bhatt DL, Lincoff AM, Gibson CM, et al., Intravenous platelet blockade with cangrelor during PCI, N Engl J Med, 2009, pp. 2330-2341, vol. 361.
Bhatt, D.L., et al., Effect of Platelet Inhibition with Cangrelor during PCI on Ischemic Events, 2013, N Engl. J. Med., pp. 1-15 Supplementary Appendix, Champion Pheonix.
Bhatt, D.L., et al., Effect of Platelet Inhibition with Cangrelor during PCI on Ischemic Events, Original Article, N Engl J Med, 2013, pp. 1303-1313, vol. 368, No. 14.

(56) References Cited

OTHER PUBLICATIONS

Boeynaems JM, Van Giezen H, Savi P, Herbert JM, P2Y receptor antagonists in thrombosis, Curr. Opin Investig Drugs, 2005, pp. 275-282, vol. 6, No. 3.
Bonello et al., "Consensus and Future Directions on the Definition of High On-Treatment Platelet Reactivity to Adenosine Diphosphate," J Am Coll Cardiol, 2010; 56:919-933.
Brilakis et al., "Perioperative Management of Patients With Coronary Stents," J Am Coll Cardiol, 2007; 49:2145-2150.
Buckland R, Judge HM, Sugidachi A, et al., Cangrelor inhibits the binding of dopidogrel and prasugrel active metabolites to the P2Y12 receptor, Eur Heart J, 2009, p. 193, vol. 30(Suppl 1).
Buckland RJ, Judge HM, Sugidachi A, et al., Reversible binding of cangrelor to the P2Y12 receptor prevents the binding of clopidogrel and prasugrel active metabolites, J Thromb Haemost, 2009, pp. 942, vol. 7(Suppl 2).
Cattaneo M., Platelet P2 receptors: old and new targets for antithrombotic drugs, Expert Rev Cardiovasc Ther, 2007, pp. 45-55, vol. 5, No. 1.
Chattaraj SC, Cangrelor antra Zeneca, Curr Opin Investig Drugs, 2001, pp. 250-255, vol. 2, No. 2.
Christensen K, Larsson R, Emanuelsson H, et al., Effects on blood compatibility in vitro by combining a direct P2Y12 receptor inhibitor and heparin coating of stents, Platelets, 2006, pp. 318-327, vol. 17, No. 5.
Cohen M, Diez, J, Levine GN, et al., Pharmacoinvasive management of acute coronary syndrome: incorporating the 2007 ACC/AHA Guidelines. The CATH (Cardic Catherization and Antithrombotic Therapy in the Hospital) Clinical Consensus Panel Report-III, J Invasive Cardiology, 2007, pp. 525-540, vol. 19, No. 12.
Dalai, A.R., et al., Brief review: Coronary drug-cloting stents and anesthesia, Can J Anesth, 2006, pp. 1230-1243, vol. 53, No. 12.
Desai, N. R., et al., The State of Periprocedural Antiplatelet Therapy After Recent Trials, Jacc: Cardiovascular Interventions, 2010, pp. 571-583, vol. 3, No. 6.
Diaz-Ricart M, Cangrelor tetradsodium, Drugs of the Future, 2008, pp. 101-110, vol. 33, No. 2.
Ding Z, Kim S, Kunapuli SP, Identification of a potent inverse agonist at a constitutively active mutant of human P2Y12 receptor, Mol Pharmaol, 2005, pp. 338-345, vol. 69, No. 1.
Dobesh et al., "Pharmacokinetics and Pharmacodynamics of Prasugrel, a Thienopyridine P2Y12 Inhibitor," Pharmacotherapy: The Journal of Human Pharmacology and Drugh Therapy, vol. 29, No. 9, Sep. 1, 2009, pp. 1089-1102.
Dovlatova et al., "Competition Between Reversible and Irreversible P2Y12 Antagonists and Its Influence on ADP-Mediated Platelet Activation," Journal of Thrombosis and Haemostasis, 5(Suppl. 2), Abstract No. S-340 (2007), only Abstract supplied.
Dovlatova N, Wijeyeratne YD, Fox SC, et al., Detection of P2Y(14) protein in platelets and investigation of the role of P2Y(14) in platelet function in comparison with the EP(3) receptor, Thromb Haemost, 2008, pp. 261-270, vol. 100.
Dovlatova NL, Jakubowski JA, Sugidachi A, et al., Rhe reversible P2Y12 antagonist cangrelor influences the ability of the active metabolites of clopidogrel and prasugrel to produce irreversible inhibition of platelet function, J Thromb Haemost, 2008, pp. 1153-1159, vol. 6.
Examination Report dated Aug. 21, 2013 in the related European Application No. 09747490.2.
Extended European Search Report dated Apr. 8, 2015 in the related European Application No. 12824414.2.
Faxon DP, Cangrelor for ACS-lessons from the Champion trials, Nat Rev Cardiol, 2010, pp. 124-125, vol. 7.
Feisler T, Gawaz M, Steinhubl SR, et al., Current strategies in antiplatelet therapy—Does identification of risk and adjustment of therapy contribute to more effective, personalized medicine in cardiovascular disease?, Pharmacol Ther, 2010, pp. 95-107, vol. 127.
Ferreiro JL, Ueno M, Angiolillo DJ, Cangrelor: a review on its mechanism of action and clinical development, Expert Rev Cardiovasc Ther, 2009, pp. 1195-1201, vol. 7.
Firstenberg, M.S., et al., P4-Safety and Efficacy of Cangrelor, An Intravenous, Short-Acting Platelet Inhibitor in Patient-equiring Cardiac Surgery, American Association for Thoracic Surgery, 2012. 92nd Ann. Mtg, pp. 309-311.
Firstenberg, M.S., et al., Safety and Efficacy of Cangrelor, an Intravenous, Short-Acting Platelet Inhibitor in Patients Requiring Coronary Artery Bypass Surgery, The Heart Surgery Forum, 2013, pp. E60-E69, vol. 16, No. 2.
Fleisher et al. ACC/AHA 2007 Guidelines on Perioperative Cardiovascular Evaluation and Care for Noncardiac Surgery. Circulation. 2007;116:e418-e500.
Norgard, N. B., Cangrelor: a novel $P2Y_{12}$ receptor antagonist, Expert Opin. Investig. Drugs, 2009, pp. 1219-1230, vol. 18, No. 8.
Nurden AT, Nurden P. Advantages of fast-acting ADP receptor blockade in ischemic heart disease (Editorial to K. Wang article p. 357),Arterioscler Thromb Vasc Biol, 2003, pp. 158-159.
Nylander S, Mattsson C, Lindahl TL, Characterisation of species differences in the platelet ADP and thrombin response, Thromb Res. 2003, pp. 65-73, vol. 111.
Oestreich, J.H., et al., Cangrelor in percutaneous coronary intervention, Expert Rev. Clin. Pharmacol., 2009, pp. 137-145, vol. 2, No. 2.
Office Action dated Jun. 11, 2013 in the related Japanese Application No. 2011-509659.
Office Action dated Jun. 30, 2015 in the related European Application No. 09747490.2.
Office Action dated Jun. 4, 2013 in the related Chinese Application No. 200980126678.1.
Oliphant, C.S., et al., Emerging $P2Y_{12}$ Receptor Antagonists: Role in Coronary Artery Disease, Current Vascular Pharmacology, 2010, pp. 93-101, vol. 8, No. 1.
Paikin, J.S., et al., New antithrombotic agents-insights from clinical trials, Nature Reviews—Cardiology, 2010, pp. 498-509, vol. 7.
Park SJ, Lee SW, Optimal management of platelet function after coronary stenting, Curr Treat Options Cardiovasc Med, 2007, pp. 37-45.
Parravicini C, Ranghino G, Abbracchio MP et al., GPR17: Molecular modeling and dynamics studies of the 3-D structure and purinergic ligand binding features in comparison with P2Y receptors, BMC Bioinformatics, 2008, pp. 1-19, vol. 9, No. 263.
Patti et al., Point-of-Care Measurement of Clopidogrel Responsiveness Predicts Clinical Outcome in Patients Undergoing Percutaneous Coronary Intervention Results of the ARMYDA-PRO (Antiplatelet therapy for Reduction of Myocardial Damage during Angioplasty-Platelet Reactivity Predicts Outcome) Study, Journal of the American College of Cardiology, 2008, vol. 52, No. 14, pp. 1128-1133.
Penz SM, Reininger AJ, Toth O, et al., Glycoprotein Ibα inhibition and ADP receptor antagonists, but not aspirin, reduce platelet thrombus formation in flowing blood exposed to atherosclerotic plaques, Thromb Haemost, 2007, pp. 135-443, vol. 97.
Phillips DR, Conley PB, Sinha U, Andre P, Therapeutic approaches in arterial thrombosis, J Thromb Haemost, 2005, pp. 1577-1589,vol. 3.
Pickard et al. Clopidogrel-associated bleeding and related complications in patients undergoing coronary artery bypass grafting. Pharmacotherapy. Mar. 2008;28(3):376-92.
Price et al., "Standard- vs High-Dose Clopidogrel Based on Platelet Function Testing After Percutaneous Coronary Intervention," JAMA. 2011;305(11):1097-1105.
Price MJ, New antiplatelet therapies in development, Am J Health Syst Pharm, 2008, pp. S11-S15, vol. 65.
R. Marcucci et al., Cardiovascular Death and Nonfatal Myocardial Infarction in Acute Coronary Syndrome Patients Receiving Coronary Stenting Are Predicted by Residual Platelet Reactivity to ADP Detected by a Point-of-Care Assay: A 12-Month Follow-Up, Circulation, vol. 119, No. 2, Jan. 20, 2009 (Jan. 20, 2009), pp. 237-242.
Raju NC, Eikelboom JW, Hirsh J. Platelet ADP-receptor antagonists for cardiovascular disease: past, present and future, Nat Clin Pract Cardiovasc Med, 2008, pp. 766-780, vol. 56, No. 12.
Ravnefjord A, Delavaux P, Tomvall J, et al., Ongoing treatment with cangrelor, but not ticagrelor, is associated with a significant reduction in the efficacy of clopidogrel in an ex-vivo canine model, J Thromb Haemost, 2009, p. 349, vol. 7 (Suppl 2).

(56) References Cited

OTHER PUBLICATIONS

Ravnefjord A, Weilitz J, Emanuelsson BM, et al., Evaluation of ticagrelor pharmacodynamic interactions with reversibly binding or non-reversibly binding P2Y12 antagonists in an ex-vivo canine. Thromb Res, 2012, pp. 622-628, vol. 130.
Rich J, Wiviott SD, New antiplatelet therapies for acute coronary syndromes, Curr Cardiol Rep, 2007, pp. 303-311, vol. 3.
Sabatine, M.S., Novel antiplatelet strategies in acute coronary syndromes, Cleve Clin J Med, 2009, pp. S8-S15, vol. 76, Supp. 1.
Schneider DJ, Sobel BE, Streamlining the design of promising clinical trials: in-vitro testing of antithmmbotic regimens and multiple agonists of platelet activation, Caron Artery Dis, 2009, pp. 175-178, vol. 20, No. 2.
Segers et al. Efficacy and safety of the oral direct factor Xa inhibitor apixabanfor symptomatic deep vein thrombosis. The Botticelli DVTdose-ranging study. Journal of Thrombosis and Haemostasis, 6: 1313-1318 (2008).
Shim et al. Effects of preoperative aspirin and clopidogrel therapy on perioperative blood loss and blood transfusion requirements in patients undergoing off-pump coronary artery bypass graft surgery. J Thorac Cardiovasc Surg. Jul. 2007;134(1):59-64.
Siddique, A., et al., New antiplatelet drugs: beyond asprin and clopidogrel, Im. J. Clin. Pract., 2009, pp. 776-789, vol. 63, No. 5.
Steg et al. Ticagrelor Versus Clopidogrel in Patients With ST-Elevation Acute Coronary Syndromes Intended for Reperfusion With Primary Percutaneous Coronary Intervention. Circulation. 2010;122:2131-2141.
Steinhubl S, Roe MT, Optimizing platelet P2YI2 inhibition for patients undergoing PCI, Cardiovasc Drug Rev, 2007, pp. 188-203, vol. 25, No. 2.
Steinhubl SR, Oh JJ, Oestreich JH, et al., Transitioning patients from cangrelor to clopidogrel: Pharmacodynamic evidence of a competitive effect, Thromb Res, 2007, pp. 527-534, vol. 121.
Storey RF, Cameron KE, Pascoe JS, et al., Potential therapeutic effect of the novel platelet adenosine diphosphate receptor (P2T) antagonist, ARC69931MX, as assessed by in vitro studies in human whole blood. A possible adjunct to aspirin therapy?, Eur Heart J, 1998, p. 493,19(Supp):54.
Storey RF, Clinical experience with antithrombotic drugs acting on purine receptor pathways, Drug Dev Res, 2001, pp. 201-212, vol. 52.
Storey RF, Judge HM, Wilcox RG, et al., Inhibition of ADP-induced p-selection expression and platelet-leukocyte conjugate formation by clopidogrel and the P2Y12 receptor antagonist AR-C69931MX but not aspirin, Thromb Res, 2002, pp. 488-494, vol. 88.
Storey RF, New developments in antiplatelet therapy, Eur Heart J. 2008, pp. D30-D37,10(SUPPD).
Storey RF, Oldroyd KG, Wilcox RG, First clinical study of the novel platelet ADP receptor (P2T) antagonist AR-C69931MX, assessing safely, tolerability and activity in patients with acute coronary syn dromes, Circulation, 1999, p. 1-170 vol. 100, No. 18.
Storey RF, Oldroyd KG, Wilcox RG, Open multicentre study of the P2T receptor antagonist AR-C69931MX assessing safety, tolerability and activity in patients with acute coronary syndromes, Thromb Haemost, 2001, pp. 401-407, vol. 85.
Storey RF, Sanderson HM, White AE, et al., The central role of the P(2T) receptor in amplification of human platelet activation, aggre gation, secretion and procoagulantactivity, Br J Haematol, 2000, pp. 925-934, vol. 110.
Storey RF, The P2Y12 receptor as a therapeutic target in cardiovascular disease. Platelets, 2001, pp. 197-209, vol. 12.
Storey RF, Variability of response to antiplatelet therapy, Eur Heart J. 2008, pp. A21-A27, 10(SUPPA).
Storey, R.F., et al., Comparison of the pharmacodynamic effects of the platelet ADP receptor antagonists clopidogrel and AR-C69931MX in patients with ischaemic heart disease, Platelets, 2002, pp. 407-413, vol. 13.
Storey, R.F., et al., Inhibition of Platelet Aggregation by AZD6140, a Reversible Oral P2YI2 Receptor Antagonist, Compared with Clopidogrel in Patients with Acute Coronary Syndromes, JACC, 2007, pp. 1852-1856, vol. 50, No. 19.
Straub, A., et al., Evidence of Platelet Activation at Medically Used Hypothermia and Mechanistic Data Indicating ADP as a Key Mediator and Therapeutic Target, JAHA, 2011, pp. 1607-1016.
Testa, L., et al., Current Conceptson Antiplatelet Therapy: Focus on the Novel Thienopyridine and Non-Thienopyridine Agents, Advances in Hematology, 2010, pp. 1-7, vol. 2010, Article ID 595934.
The Extended European Search Report dated Apr. 11, 2012 in the related European Application No. 09747490.2.
Turpie et al. Rivaroxaban versus enoxaparin for thromboprophylaxis after total knee arthroplasty (RECORD4): a randomised trial. Lancet. May 16, 2009;373(9676):1673-80.
Ueno, M., et al., Update on the clinical development of cangrelor, Expert Rev Cardiovasc Ther, 2010, pp. 1069-1077, vol. 8, No. 8.
Van Giezen JJ, Humphries RG, Preclinical and clinical studies with selective reversible direct P2Y12 antagonists, Semin Thromb Hemost, 2005, pp. 195-204, vol. 31, No. 2.
Van Giezen JJ, Optimizing platelet inhibition, Eur Heart J, 2008, pp. D23-D29, vol. 10(Suppl D).

\* cited by examiner

Figure 1

Figure 3: Chart of an Exemplary Method

MAINTENANCE OF PLATELET INHIBITION DURING ANTIPLATELET THERAPY This invention is a continuation of U.S. application Ser. No. 14/195,798 filed on Mar. 3, 2014, which has issued as U.S. Pat. No. 10,231,987 on Mar. 19, 2019, which is a continuation of U.S. application Ser. No. 13/209,271 filed on Aug. 12, 2011, now abandoned, which is a continuation-in-part of U.S. application Ser. No. 12/990,332 filed on Oct. 29, 2010, which has issued as U.S. Pat. No. 8,871,736 on Oct. 28, 2014, which claims priority to PCT/US09/043820 filed on May 13, 2009, claiming which claims priority to U.S. provisional application No. 61/127,424 filed on May 13, 2008. Each of the above referenced applications is incorporated herein by reference.

FIELD OF THE INVENTION

The instant invention relates to the field of platelet inhibition, and in particular to methods of maintaining or reducing platelet activity in patients undergoing an invasive procedure.

BACKGROUND OF THE INVENTION

Anti-platelet therapy has been shown to reduce clinical ischemic events and improve outcomes for acute coronary syndrome (ACS) patients. Currently, the approved anti-platelet products include aspirin and thienopyridines, such as clopidogrel and ticlopidine. One of the most widely prescribed thienopyridines is clopidogrel, which is also known as Plavix®.

Thienopyridines such as clopidogrel irreversibly inhibits $P2Y_{12}$ receptors which play an active role in platelet activation. In the normal state, when blood vessels are damaged, platelet activation mediated by $P2Y_{12}$ receptors play an important role to arrest bleeding at the site of injury. In a diseased state, platelet activation leads to vascular occlusion and ischemic damage. Thus, $P2Y_{12}$ receptors antagonists play a key role in antiplatelet therapy in assisting to prevent coronary artery disease and for the immediate treatment of ACS and percutaneous coronary intervention (PCI).

Physicians often prescribe dual anti-platelet therapy, which include aspirin and a thienopyridine, such as clopidogrel for patients who have been diagnosed with ACS or for patients who are showing symptoms associated with ACS as a first line treatment. Pending further examinations, these patients may continue with this treatment or receive other treatments such as coronary artery bypass grafting (CABG) and PCI. Consistent with this practice, current American College of Cardiology/American Heart Association (ACC/AHA) guidelines recommend immediate initiation of dual anti-platelet therapy of clopidogrel and aspirin after a patient is diagnosed with ACS. Similarly, patients that have received a bare metal stent or drug-eluting stent are also put on the dual clopidogrel and aspirin therapy for an extended period of time to prevent an ischemic event. For instance, a post hoc analysis of a blinded, placebo-controlled trial suggest a benefit of platelet activity inhibition in terms of decreased thrombotic events prior to CABG (Fox K A et. al, *Circulation*. 2004; 110; 1201-08). For many patients, this dual anti-platelet therapy provides tremendous clinical benefits, and minimizes the risks of ischemic events, such as heart attack and stroke.

Dual anti-platelet therapy, however, has drawbacks. Cessation of clopidogrel may increase the incidence of ischemic events in the short-term due to a "rebound" effect of platelet activation (Brilakis E S et al, *J Am Coll Cardiol*. 2007 Jun. 5; 49(22):2145-50; Ho P M et al, *JAMA*. 2008 Feb. 6; 299(5):532-9).

In addition patients receiving dual anti-platelet therapy experience an increased incidence of blood transfusions and bleeding complications while undergoing surgery and other invasive procedures. This is particularly true for ACS patients who often receive surgery, such as CABG and PCI, and other invasive procedures, such as implantation of a bare metal stent (BMS) or drug-eluting stent (DES). Because aspirin and thienopyridines are irreversible, long-acting platelet antagonists reversal of the inhibition of platelet function occurs only as new platelets are generated and therefore even after discontinuation, their effect can lasts several days before being completely eliminated.

Thus, for patients under dual therapy who also require surgery such as CABG sustained platelet inhibition poses an unacceptable risk of bleeding. Consequently, it has been recommended by the ACC/AHA and the Society of Thoracic Surgeons (STS) guidelines to cease thienopyridine therapy prior to undergoing non-emergent cardiac surgical procedures to minimize bleeding risks. Thus, patients are often required to stop dual anti-platelet therapy and wait for five to seven days before any invasive procedures can be performed.

On the other hand, even though clopidogrel treatment prior to CABG does increase bleeding due to its irreversibility, platelet P2Y12 inhibition does appear to prevent ischemic events in patients requiring CABG. As a result, physicians often face the difficult choice of discontinuing clopidogrel and aspirin prior to surgery and risking a potential ischemic event in the unprotected perioperative period or delaying surgery until the time at which clopidogrel is no longer required.

Currently, no ultra short-acting platelet inhibitors are available that allow maintenance of platelet inhibition before an invasive procedure without increasing bleeding complications at the time of an invasive procedure. Potentially, effective platelet inhibition with an ultra short-acting platelet inhibitor during the period of clopidogrel withdrawal may protect patients from ischemic events and also preserve normal hemostasis at the time of surgery.

Therefore, a need exists for a new therapy for patients who are undergoing surgery (this includes therapy prior to, during, and post) or other invasive procedures, and who have a need for anti-platelet therapy. This new therapy maintains platelet inhibition at acceptable levels while allowing for rapid restoration of platelet function after discontinuation so that patients may undergo surgical procedures without increasing the risk of bleeding complications.

In addition, a need exists for a new therapy for patients who, for whatever reason, cannot be administered thienopyridines, such as clopidogrel or Plavix®, or cannot receive orally administered antiplatelet therapies.

SUMMARY OF THE INVENTION

As shown herein, the present invention describes compositions and methods of maintaining or reducing platelet activity in a patient prior to the patient undergoing an invasive procedure by administering an effective amount of short-acting $P2Y_{12}$ inhibitor.

In one aspect of this invention methods are described for administering an effective amount of a short-acting $P2Y_{12}$ inhibitor to maintain or reduce platelet activity in a patient before an invasive procedure, in a patient previously treated with long-acting irreversible platelet inhibitors without an increase risk in bleeding.

In a related embodiment of this method, other therapeutic agents are administered concurrently with the reversible, short-acting $P2Y_{12}$ inhibitor.

In another related embodiment of this method, the risk of bleeding is not increased.

In another aspect of this invention, a short-acting $P2Y_{12}$ inhibitor is use to maintain or reduce platelet activity in patients perioperatively where oral antiplatelet therapy is contraindicated. The reversible, short-acting $P2Y_{12}$ inhibitor can be administered to a patient as a bolus and or a continuous intravenous infusion. In another aspect of this invention, methods are described where an effective amount of a short-acting $P2Y_{12}$ inhibitor is administered to sufficiently reduce or maintain at least 60% platelet inhibition or $P2Y_{12}$ reaction unit (PRU) PRU values less than 240 prior to the patient undergoing an invasive procedure.

In a related embodiment to this method, the short-acting $P2Y_{12}$ inhibitor is discontinued thereby allowing platelet activity to return to pre-administration levels as measured by PRU being greater than 240.

In yet another aspect of the present invention, methods are described for administering a reversible, short-acting $P2Y_{12}$ inhibitor to a patient who was previously administered a thienopyridine, and ceasing administration of the short-acting $P2Y_{12}$ inhibitor wherein the PRU levels is similar to pre-administration levels of the short-acting $P2Y_{12}$ inhibitor, prior to said patient undergoing an invasive procedure.

In another aspect of this invention, a method of treating or preventing thrombosis is described by administering a short-acting $P2Y_{12}$ inhibitor to a patient previously treated with a long-acting irreversible platelet inhibitor, where the risk of bleeding is not increased.

In another aspect of this invention, an intravenous pharmaceutical composition of cangrelor is described for maintaining or reducing platelet inhibition.

In another aspect of this invention, a method for preparing an intravenous cangrelor composition for inhibiting platelet activity by combining cangrelor with mannitol, sorbitol and intravenously administrable excipient for maintaining PRU values at a certain level.

BRIEF DESCRIPTION OF THE FIGURES

Understanding of the present invention will be facilitated by consideration of the following detailed description of the embodiments of the present invention taken in conjunction with the accompanying drawings, in which like numerals refer to like parts and in which:

FIG. 4 is a table of the studied assessments by time point.

DETAILED DESCRIPTION

It is to be understood that the figures and descriptions of the present invention have been simplified to illustrate elements that are relevant for a clear understanding of the present invention, while eliminating, for the purpose of clarity, many other elements found in typical antiplatelet therapies. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

The present invention provides a method for inhibiting platelet activities in patients prior to undergoing an invasive procedure.

The methods described in the present invention maintains platelet inhibition at acceptable and targeted levels, while allowing for rapid restoration of platelet function after discontinuation of the drug therapy so that patients may undergo invasive procedures without increasing the risk of bleeding complications.

The described methods can be used for patients in need of treatment to reduce or maintain platelet inhibition. Preferably the described methods can be used in patients at risk of thrombotic events. More preferably the embodiments of the present invention are directed to patients diagnosed with symptoms of stable or unstable angina, vascular ischemic events, atherosclerosis, acute coronary syndrome, as well as STEMI or N-STEMI. The described methods can also be used for patients having previously received a stent, such as a bare metal stent or a drug-eluting stent, for the treatment or prevention of stent thrombosis. While the present invention is generally targeted for use with human patients, the described methods can be used on any living animal.

The present invention further provides a method for reducing or maintaining adequate $P2Y_{12}$ inhibition with rapid reversibility upon discontinuation of long-acting irreversible platelet inhibitors prior to patients undergoing invasive procedures without increasing the risk of bleeding complications.

Definitions

Long-acting $P2Y_{12}$ inhibitors refer to compounds which inhibit $P2Y_{12}$ receptor activities, having a slow on-set and long elimination half-life. Examples of long-acting $P2Y_{12}$ inhibitors are typically formulated as oral dosage forms. One example of long-acting $P2Y_{12}$ inhibitor is long-acting irreversible $P2Y_{12}$ inhibitors. Examples of long-acting irreversible $P2Y_{12}$ inhibitors include thienopyridines. Examples of thienopyridines, include without limitation clopidogrel, ticloridine, and prasugrel and such other compounds having similar properties. Clopdogrel is a pro-drug that requires metabolism for conversion to the active metabolite.

Short-acting reversible, $P2Y_{12}$ inhibitors refer to compounds which inhibits $P2Y_{12}$ receptor activities, having a fast onset time and a relatively short metabolism rate as compared to those of thienopyridines. Examples of a short-acting, reversible $P2Y_{12}$ inhibitor include, without limitations, cangrelor, ticagrelor and PRT060128. It should be noted that the present invention is not limited to these examples. Additional compounds that have similar properties may also be used in the present invention.

One particularly preferred example of a reversible, short-acting $P2Y_{12}$ inhibitor is cangrelor. Cangrelor is a potent, direct, and reversible antagonist of the platelet $P2Y_{12}$ receptor. Cangrelor has a half life of approximately less than 10 minutes, allowing for a return to normal platelet function in a very short period of time upon discontinuation of the drug. By reducing the need for a compound to be metabolized for activity, and by having a relatively short half life, reversible, short-acting $P2Y_{12}$ inhibitors are considered "reversible", meaning that full platelet functionality may return rather quickly as compared to thienopyridines.

The binding of cangrelor to the $P2Y_{12}$ receptor inhibits platelet activation as well as aggregation when mediated in whole or in part via this receptor. Cangrelor can be derived completely from synthetic materials, and is an analogue of adenosine triphosphate (ATP), the natural antagonist found in humans specific to the $P2Y_{12}$ receptor sites.

The chemical structure for cangrelor is depicted below as Formula I.

Formula I

Cangrelor is clinically well tolerated and safe and does not react with aspirin, heparin or nitroglycerin. Unlike orally dosed theinopyridines, cangrelor can be administered intravenously and binds directly to P2Y12 receptor sites of platelets. In each of the embodiments of the present invention, the term "cangrelor" encompasses the compound of Formula I as well as tautomeric, enantiomeric and diastereomeric forms thereof, and racemix mixtures thereof, other chemically active forms thereof, and pharmaceutically acceptable salts of these compounds, including a tetrasodium salt. These alternative forms and salts, processes for their production, and pharmaceutical compositions comprising them, are well known in the art and set forth, for example, in U.S. Pat. No. 5,721,219. Additional disclosure relevant to the production and use of cangrelor may be found in U.S. Pat. Nos. 5,955,447, 6,130,208 and 6,114,313, as well as in U.S. Appln. Publication Nos. 2006/0270607 and 2011/0112030.

Invasive procedures means any technique where entry to a body cavity is required or where the normal function of the body is in some way interrupted by a medical procedure and/or treatment that invades (enters) the body, usually by cutting or puncturing the skin and/or by inserting instruments into the body. Invasive procedures can include coronary artery bypass grafting (CABG), orthopedic surgeries, urological surgeries, percutaneous coronary intervention (PCI), other general invasive procedures, such as endarterectomy, renal dialysis, cardio-pulmonary bypass, endoscopic procedures or any medical, surgical, or dental procedure that could result in excessive bleeding or hemorrhage to the patient.

Perioperative means the period of a patient's invasive procedure which can occur in hospitals, surgical centers or health care providers' offices. Perioperative includes admission, anesthesia, surgery, to recovery.

Thrombosis is the formation of a blood clot (thrombus) inside a blood vessel obstructing the flow of blood through the circulatory system. When a blood vessel is injured, the body uses platelets and fibrin to form a blood clot to prevent blood loss. Some examples of the types of thrombosis include venous thrombosis which includes deep vein thrombosis, portal vein thrombosis, renal vein thrombosis, jugular vein thrombosis, Budd-Chiari syndrome, Paget-Schroetter disease, cerebral venous sinus thrombosis, cerebral venous sinus thrombosis and arterial thrombosis which includes, stroke and myocardial infarction.

Dosage and Administration

As used herein, the terms "dose", "dosage", "unit dose", "unit dosage", "effective dose", "effective amount" and related terms refer to physically discrete units that contain a predetermined quantity of cangrelor, calculated to produce a desired therapeutic effect. These terms are synonymous with the therapeutically effective amounts and amounts sufficient to achieve the stated goals of the methods disclosed herein.

When administered as an intravenous (IV) formulation, a pharmaceutical composition comprising cangrelor may be administered as a bolus, as a continuous infusion, or as a bolus followed by a continuous infusion. When administered as a bolus, a dose of about 5, 10, 15, 20, 25, 30, 35, 40, 45, 50, 55, 60, 65, 70, 75, 80, 85, 90, 95 or 100 µg/kg cangrelor, or more, is administered to the patient. In preferred embodiments, between about 20 µg/kg and about 40 µg/kg cangrelor is administered, more preferably about 30 µg/kg. When administered as a continuous infusion, cangrelor may be administered at about 0.1, 0.5, 0.75, 1, 2, 3, 4, 5, 6, 7, 8, 9, 10, 15, 20, 25, 30 µg/kg/min, or more to the patient. In preferred embodiments, between about 0.1 and about 5 µg/kg/min cangrelor is administered, more preferred is administration of cangrelor in the range of about 0.5 µg/kg/min to about 2 µg/kg/min. Even more preferred is a dosage range of cangrelor at about 0.5 µg/kg/min to about 1 µg/kg/min. The skilled artisan will understand that different bolus and intravenous dosages from those set forth here may be administered based on the particular characteristic of the patient. Thus, the dosage amount can be varied from the dosage amount presently described, however, the dosage given must be sufficient to reduce or maintain the PRU values below about 240 as measured by VerifyNow®.

In addition, the skilled artisan will understand that the exact amount of reversible short-acting $P2Y_{12}$ inhibitor to be administered to a patient will vary depending on the degree of platelet activity inhibition that is sought. For example, the amount of reversible short-acting $P2Y_{12}$ inhibitor to be administered to a patient during an invasive procedure that will result in bleeding may be much less than the amount that would be administered when such a procedure is not being performed.

The dosage of the reversible short-acting $P2Y_{12}$ inhibitor may be administered as a continuous intravenous infusion or it may be administered in discrete does, such as between 1 and 48 doses, or more, per 24 hour period. The dosage of the reversible short-acting $P2Y_{12}$ inhibitor may vary over time, with a lower dosage being initially administered, followed by an increased dosage for a sustained period of time, with an optional decrease in the dosage prior to complete cessation of administration of the reversible short-acting $P2Y_{12}$ inhibitor. Such a dosing regime may be used in conjunction with the concurrent cessation of thienopyridine and/or aspirin treatment and beginning of reversible short-acting $P2Y_{12}$ inhibitor. Such dosing regime can also ensure a constant level of platelet activity inhibition.

In other forms, a reversible, short-acting $P2Y_{12}$ inhibitor can be administered at a daily dose of from 0.1 mg to 1000 mg, which may be in divided doses e.g. up to 6 times per day.

The total amount of reversible, short-acting $P2Y_{12}$ inhibitor that may be administered to a subject may be between about 0.01 and 1000 mg per 24 hour period, with exemplary totals of about 0.5, 0.75, 1.0, 1.25, 1.5, 1.75, 2.0 and 2.5 mg per 24 hour period.

In each of the embodiments where the pharmaceutical composition is administered as continuous intravenous infusion, the infusion may continue for at least about 2 days to about 7 days. The skilled artisan will understand that the period of time over which the pharmaceutical composition is administered may be shorter or longer than the indicated times due to the particular characteristics of a patient. Administration of a reversible, short-acting $P2Y_{12}$ inhibitor can be made several days to several hours prior to the invasive procedure. One example is to administer a reversible, short-acting $P2Y_{12}$ inhibitor about 7 days to about 1 hour prior to an invasive procedure. To maintain platelet inhibition, the reversible short-acting $P2Y_{12}$ inhibitor should be administered within about 2 days to about 7 days of ceasing administration of the long-acting platelet inhibitor. A further example is to administer the reversible short-acting $P2Y_{12}$ inhibitor within about 3 days of ceasing administration of the long-acting platelet inhibitor. Discontinuation of the reversible short-acting P2Y12 inhibitor can be performed about 1 to 6 hours before a surgical procedure. It should be noted that the duration for administering a reversible, short-acting $P2Y_{12}$ inhibitor often vary depending on which reversible, short-acting $P2Y_{12}$ inhibitor is used and the particular characteristic of the patient. One skilled in the art can vary the duration of administration so long as platelet inhibition as measured by VerifyNow® is below about 240.

Reversible, short-acting $P2Y_{12}$ inhibitors, such as cangrelor, ticagrelor or PRT060128, can be administered using any of the various methods and delivery systems known to those skilled in the art. The administering can be performed, for example, intravenously, orally, via implant, transmucosally, transdermally, intramuscularly, intrathecally, and subcutaneously. According to one preferred embodiment, a reversible, short-acting $P2Y_{12}$ inhibitor may be administered intravenously. It is contemplated that the reversible, short-acting $P2Y_{12}$ inhibitor can be administered intravenously in accordance with the present invention during surgery, when the patient is comatose, or any other such scenario where the oral administration of the inhibitor is prohibited.

In the case of administering the therapy prior to surgery in accordance with one embodiment of the present invention, such use allows patients to undergo surgery or other invasive procedures without excessive perioperative bleeding. For example, as described herein, cangrelor infusion can maintain platelet inhibition levels of approximately greater than or equal to about 60% after discontinuation of clopidogrel without an increase in bleeding risk and before the invasive procedure begins.

In addition to the pharmaceutical compositions of the present invention comprising cangrelor, the skilled artisan will understand that additional therapeutic agents may be used in combination with cangrelor. By way of non-limiting examples, compounds such as aspirin, bibalirudin unfractionated heparin, low molecular weight heparin, fondaprinux sodium, warfarin, coumarins, thromboblytics such as streptokinase, Alteplase, Reteplase, urokinsc urokinase, Tenecteplase, glycoprotein IIb/IIIa inhibitors such as eptifibatide, abciximab, tirofiban, epsilon amino-caproic acid, and tranexamic acid, can be used as concomitant medications.

Measurement of Platelet Activity

Assessment of platelet function can be determined by use of the VerifyNow® assay of which the System User Manual (Accumetrics, San Diego, Calif., 2009) is incorporated by reference in its entirety. The VerifyNow® $P2Y_{12}$ assay is a point of care device for the assessment of the level of inhibition of platelet activation specifically designed for patients exposed to thienopyridines. It should be understood that any assay system for determining levels of inhibition of platelet activation can be used, as understood by those having skill in the art. Blood samples for the VerifyNow® $P2Y_{12}$ assay can be collected into Greiner Bio-One Vacuette partial fill blood collection tubes (2 mL fill volume) containing 3.2% citrate, or by other suitable means.

The VerifyNow® $P2Y_{12}$ assay is a rapid platelet-function cartridge-based assay that activates platelets using adenosine diphosphate (ADP), but also uses prostaglandin E1 to suppress the ADP-induced P2Y1-mediated increase in intracellular calcium levels to increase the specificity of the test for inhibition of the $P2Y_{12}$ receptor. The test cartridge contains a lyophilized preparation of human fibrinogen coated beads, platelet agonist, buffer and preservative. Fibrinogen-coated microparticles are used to bind to available platelet receptors. When the activated platelets are exposed to the fibrinogen-coated microparticles, agglutination occurs in proportion to the number of available platelet receptors. The whole-blood citrate mixture is added to the cartridge, and agglutination between platelets and coated beads is recorded. The VerifyNow® $P2Y_{12}$ device is a turbidimetric optical detection system, which measures platelet induced aggregation as an increase in light transmittance. VerifyNow® $P2Y_{12}$ testing can be used at any time point as described herein to assess the level of inhibition of platelet activity.

Assay results are expressed in $P2Y_{12}$ reaction units (PRU) (VerifyNow® System User Manual (Accumetrics, San Diego, Calif., 2009)). High platelet reactivity, as assessed by VerifyNow® $P2Y_{12}$ assay was defined as a PRU value greater than 240. The lower the PRU value the greater the inhibition of the $P2Y_{12}$ receptor resulting in reduction of the platelet activity. For the methods described in this invention, the PRU level is preferably maintained during the period of cangrelor administration at 240 or less. In a preferred embodiment of the present invention, the dose of cangrelor was 0.75 µg/kg/min. This dose was maintained for about 2 to about 7 days. PRU values in the patients were less than or equal to 240.

It would be understood by those skilled in the art that increasing the concentration of cangrelor infusion will result in a decrease in PRU values and an increase in the percent platelet inhibition. It is therefore preferred to measure PRU values during the course of cangrelor infusion and to adjust the infusion rate accordingly.

Pharmaceutical Compositions

In each aspect and embodiment of the present invention, short-acting reversible platelet inhibitor is administered to a patient in the form of a pharmaceutical composition comprising the active ingredient and, optionally, a pharmaceutically acceptable carrier, diluent and/or excipient. Thus, the present invention encompasses: (i) a pharmaceutical composition comprising cangrelor, and a pharmaceutically acceptable carrier, diluent and/or excipient;

Suitable carriers and diluents are well known to those skilled in the art and include saline, such as 0.9% NaCl, buffered saline, dextrose (e.g., 5% dextrose in water), water, Water-for-Injection (WFI), glycerol, ethanol, ringer's solution, propylene glycol, polysorbate 80 (Tween-80), 0.002% polysorbate 80 (Tween-80), poly(ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin, hydrophilic and hydrophobic carriers, and combinations thereof. Hydrophobic carriers include, for example, fat emulsions, lipids, PEGylated phospholipids, polymer matrices, biocompatible polymers, liposheres, vesicles, particles, and liposomes. Excipients included in a pharmaceutical composition have different purposes depending, for example on the nature of the drugs, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavouring agents, coloring agents, administration aids, and combinations thereof.

The pharmaceutical composition may contain common carriers and excipients, such as cornstarch or gelatin, lactose, sucrose, microcrystalline cellulose, kaolin, mannitol, sorbiton, dicalcium phosphate, sodium chloride, alginic acid, croscarmellose sodium, and sodium starch glycolate.

The pharmaceutical compositions of the present invention may be formulated, for example, for oral, sublingual, intranasal, intraocular, rectal, transdermal, mucosal, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection or infusion of drug formulations can be used to effect such administration. In noted aspects and embodiments of the present invention, administration of the pharmaceutical compositions is via parenteral administration, preferably intravenous administration.

In intravenous (IV) administration, a sterile formulation of the pharmaceutical compositions of the present invention and optionally one or more additives, including solubilizers or surfactants, can be dissolved or suspended in any of the commonly used intravenous fluids and administered by infusion. Intravenous fluids include, without limitation, isotonic infusion media such as physiological saline, 0.9% NaCl, phosphate buffered saline, 5% dextrose in water, 0.002% polysorbate 80 (Tween-80) in water or Ringer's solution.

Pharmaceutical compositions comprising cangrelor of the present invention include pharmaceutical compositions comprising from about 0.1 to about 50 mg/ml of cangrelor. Particular examples of pharmaceutical compositions comprising cangrelor include the following: (i) cangrelor at a concentration of about 0.1, 0.5, 1, 2, 3, 4, 5, 6, 7, 8, 9, or 10 mg/mL in 0.9% NaCl, and (ii) cangrelor at a concentration of about 0.1, 0.5, 1, 2, 3, 4, 5, 6, 7, 8, 9, or 10 mg/mL in 5% dextrose in water. The pharmaceutical composition may further comprise a pharmaceutically acceptable carrier or diluent such as sorbitol and mannitol.

One method for preparing a cangrelor composition includes dissolving 50 mg lyophilized cangrelor or its pharmaceutically acceptable salt by injecting 5 ml sterile water into a 10 ml vial containing cangrelor or its pharmaceutically acceptable salt thereof, preparing an intravenous bag by immediately adding the dissolved cangrelor to an intravenous bag containing saline solution in volumes such as 250 ml, 500 ml, or 1000 ml of saline solution and mixing the intravenous bag thoroughly for administration. Cangrelor compositions should be prepared immediately prior to administration via infusion. It is within the skilled in the art to vary the volume of saline and amount of cangrelor in the exemplary method described above to achieve the dosage amount described in the preferred embodiments.

The described methods can be used for patients diagnosed with symptoms such as stable or unstable angina, vascular ischemic events, atherosclerosis, acute coronary syndrome, including STEMI or N-STEMI. The described methods can also be used for patients having previously received a stent, such as a bare metal stent or a drug-eluting stent, and the treatment or prevention of stent thrombosis.

The described methods can be used for a patient before, during, and after an invasive procedure, such as coronary artery bypass grafting, orthopedic surgeries, urological surgeries, percutaneous coronary intervention, other general invasive procedures, such as endarterectomy, renal dialysis, cardio-pulmonary bypass, endoscopic procedures or any medical, surgical, or dental procedure that could potentially lead to excessive bleeding or hemorrhage.

Further, the described methods of the present invention can be used in a patient who cannot be orally administered therapies and, for whatever reason, cannot be administered long lasting thienopyridines, such as clopidogrel or Plavix®.

Results of the Methods

To determine how to administer a reversible, short-acting $P2Y_{12}$ inhibitor or the amount of a reversible, short-acting $P2Y_{12}$ inhibitor to be administered, the pharmacokinetic profile of the reversible, short-acting $P2Y_{12}$ inhibitor can be analyzed using the methods well-known to a person skilled in the art.

For example, the pharmacokinetics of cangrelor has been shown to be substantially linear, and its steady-state plasma concentrations can be achieved in less than approximately 5 minutes following the administration of an intravenous infusion.

Figure 1:
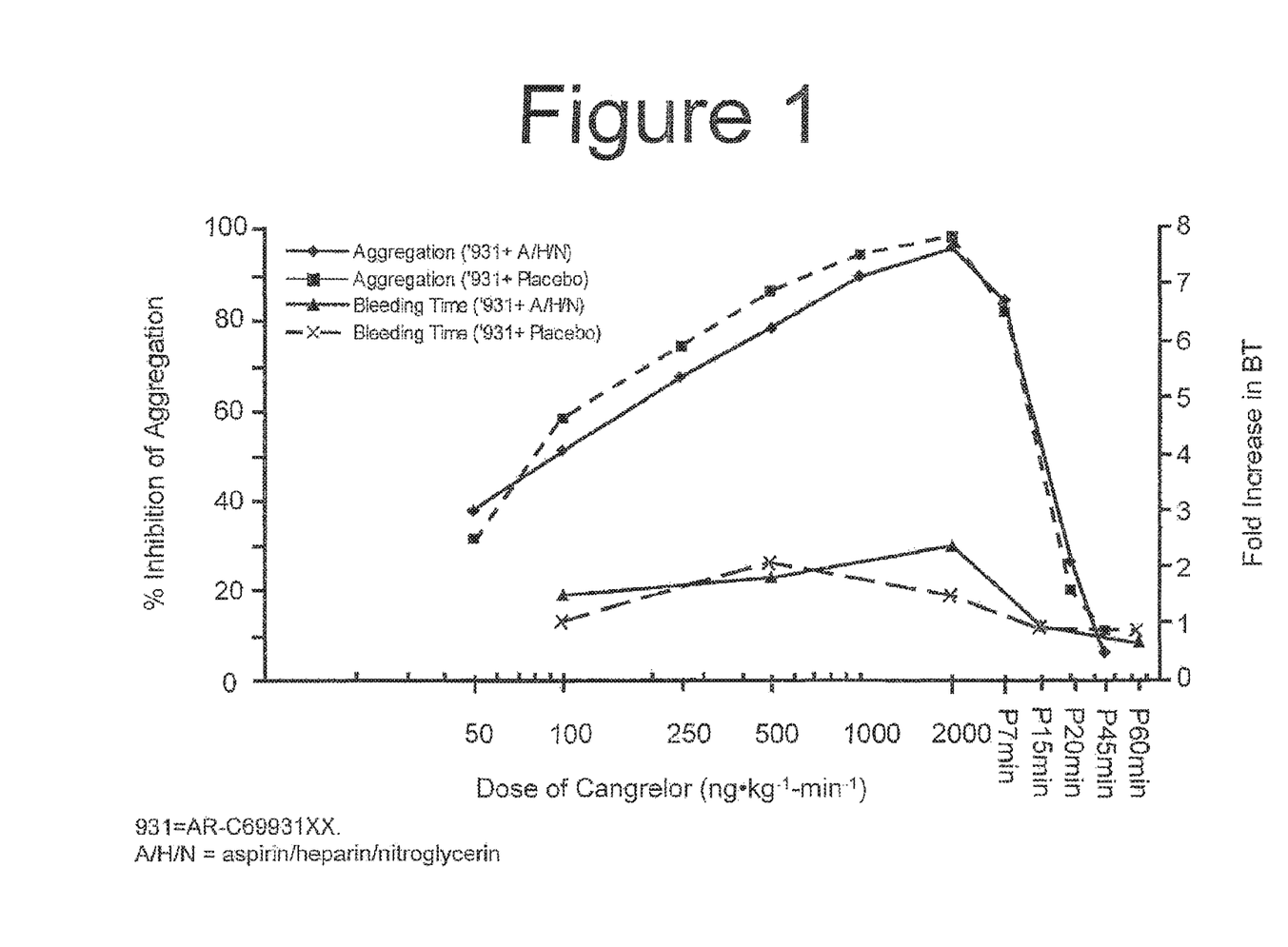
FIG. 1 is a graphical presentation of the percent inhibition of ADP-induced platelet aggregation and effect on bleeding time.

Cangrelor produced potent inhibition of ADP-induced platelet aggregation ex vivo with 1050 7.72+/−1.95 ng/mL. As may be seen in FIG. 1, over 80% inhibition was achieved at doses of about 0.5 μg/kg/min and above. Inhibition by cangrelor was rapidly reversible and platelet aggregatory response restored close to baseline within one hour of stopping the infusion. An infusion dose of approximately about 0.75 μg/kg/min of cangrelor can also maintain adequate antiplatelet activity during infusion in the targeted patient prior to an invasive procedure.

It has been determined that consistent and complete platelet inhibition can be maintained throughout cangrelor infusion with full recovery of platelet function within approximately one hour of infusion cessation. Clopidogrel administration at the termination of cangrelor infusion may lead to the expected degree of platelet inhibition, which may be measured by P-selectin expression, electrical impedance and light transmittance aggregometry.

Example 1

Figure 2:
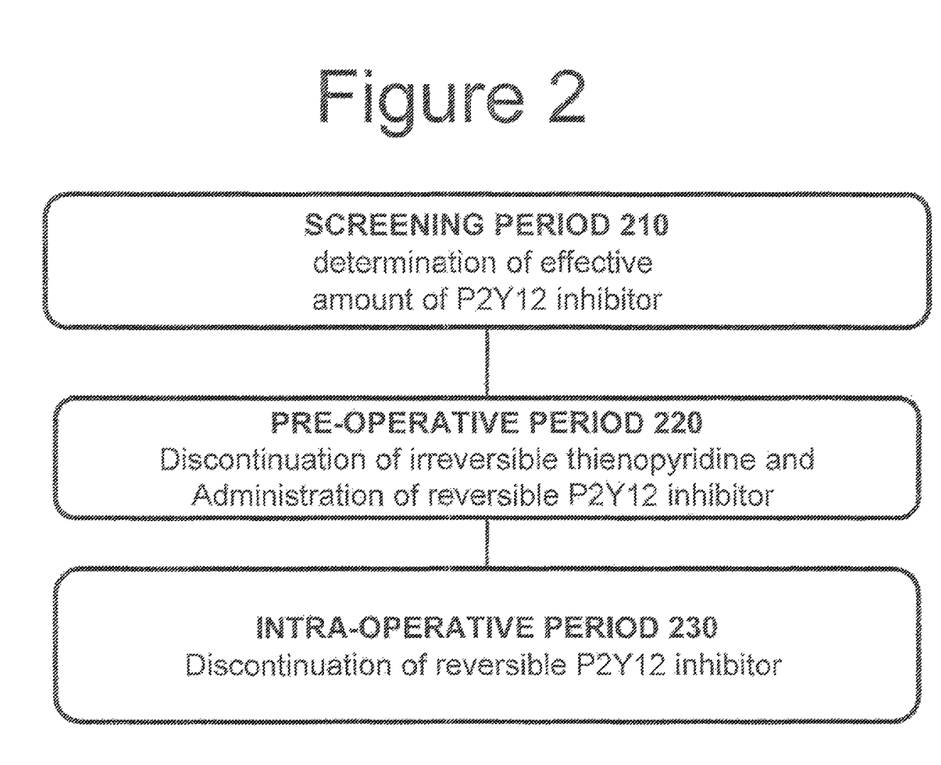
FIG. 2 is a flow chart of the time periods through which the present invention is performed.

Without limitations, FIG. 2 provides a brief summary as to how the methods described in the present invention may be used in a patient in need thereof. It should be understood that the method of the present invention is not limited to the procedure described in FIG. 2.

FIG. 2, shows a screening period 210 used for determining the dosage necessary for achieving platelet inhibition greater than a predetermined level, for example, of approximately 60%. A pre-operative period 220 of up to approximately 7 days prior to surgery can be used for administration of a reversible, short-acting $P2Y_{12}$ inhibitor. An intra-operative period 230 lasting from the discontinuation of the reversible, short-acting $P2Y_{12}$ inhibitor to the end of surgery can be used.

During the screening period 210, the dosage of a reversible, short-acting $P2Y_{12}$ inhibitor, necessary to achieve platelet inhibition greater than approximately 60% can be determined. Other suitable levels of percent inhibition are approximately 65, 70, 75, 80, 85, 90, 95 and 100%. For example, intravenous infusion of a reversible, short-acting $P2Y_{12}$ inhibitor can be administered to a patient in doses typically ranging from about 0.5 µg/kg/min to about 5.0 µg/kg/min, preferably about 0.5 µg/kg/min to about 2.0 µg/kg/min and particularly at doses of 0.5 µg/kg/min, 0.75 µg/kg/min, 1.0 µg/kg/min, 1.5 µg/kg/min and 2.0 µg/kg/min, until measured platelet inhibition is greater than the predetermined level. Smaller or larger doses may also be used as needed to achieve the required level of platelet inhibition.

Optionally, the dosage of a reversible, short-acting $P2Y_{12}$ inhibitor for any particular patient can also be determined ahead of time, so as to reduce the need to give multiple doses to achieve the required level of platelet inhibition. In all instances where measurement of platelet inhibition is needed, a baseline value should be obtained to accurately determine when acceptable levels have been reached.

During pre-operative period 220, administration of a reversible, short-acting $P2Y_{12}$ inhibitor can be initiated the day the decision is made to discontinue the long-acting irreversible platelet inhibitor and may be continued throughout pre-operative period 220. In another embodiment, administration of cangrelor can be made within 3 days of ceasing administration of the long-acting irreversible platelet inhibitor.

A patient can undergo CABG within 3 days of ceasing administration of the long-acting irreversible platelet inhibitor. The dose of such a reversible, short-acting $P2Y_{12}$ inhibitor can remain constant or can be periodic during the treatment period. Preferably the dosage of cangrelor remain continuous during the treatment period of about 2 to about 7 days. Treatment with reversible, short-acting $P2Y_{12}$ inhibitor may then be terminated from about one hour to about 6 hours before an invasive procedure.

Also during pre-operative period 220, any number of procedures and/or tests can be performed in conjunction with the present invention, such as hemoglobin, hematocrit, white blood cells, and platelet count testing; serum creatinine testing; measurement of inhibition of platelet activation; and assessment of concomitant medications, adverse events, serious adverse events and other various clinical endpoints. Additionally, procedures such as CK and CK-MB and VerifyNow® $P2Y_{12}$ assays, for example, can be performed within 24 hours prior to surgery.

During intra-operative period 230, administration of a reversible, short-acting $P2Y_{12}$ inhibitor can be stopped between from about at least 1 hour and up to approximately 3 hours prior to administration of anesthesia for surgery. Basic standard of care treatment is used for the surgical period as understood by those having skill in the art. Collection of concomitant medications and assessments of adverse events, serious adverse events and clinical endpoints can also be performed during this period as needed.

Example 2

Figure 3:
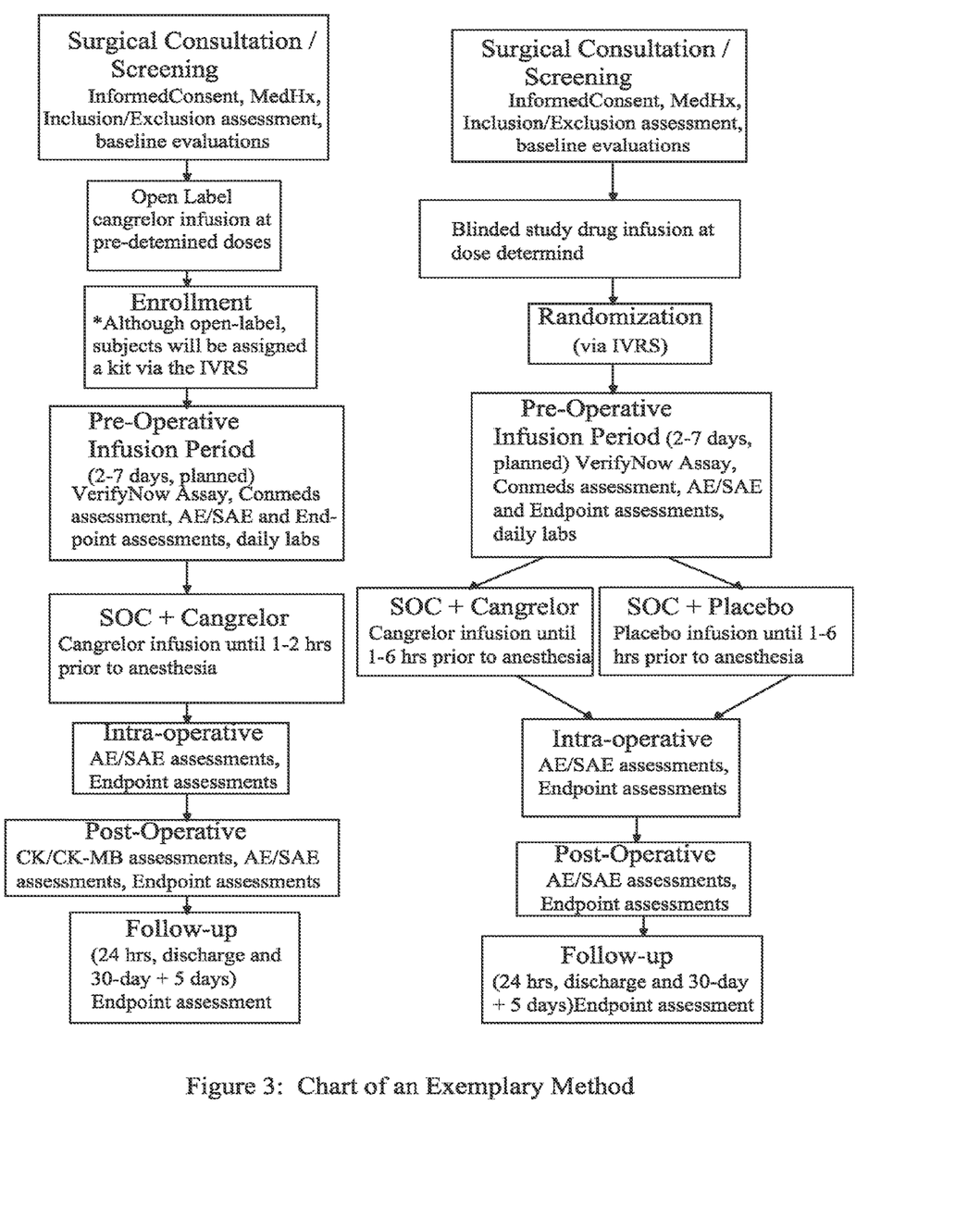
FIG. 3 is a flow chart of a study demonstrating an exemplary method.

FIG. 3 describes is a non-limiting exemplary method for maintaining or reducing platelet activity in patients who were previously treated with thienopyridine prior to undergoing an invasive procedure such as CABG.

In FIG. 3, a total of 207 patients were studied. Patients were included in from this study if they met all of the following criteria: 1. Must be at least 18 years of age; 2. Anticipate non-emergent coronary artery bypass graft (CABG) surgery, either "onpump" or "off-pump," no sooner than 48 hours from randomization but no longer than 7 days from randomization, with patient to remain hospitalized until planned CABG; 3. Have received a thienopyridine (at least 75 mg of clopidogrel, 500 mg ticlopidine, or 10 mg prasugrel) within 72 hours prior to enrollment in the study for either: the treatment of an acute coronary syndrome, regardless of time from ACS, and/or as long-term preventative therapy following drug-eluting or bare metal stent treatment.

Patients were excluded from the study if any of the following exclusion criteria applied prior to randomization: 1. Confirmed or suspected pregnancy (if woman of childbearing potential) or lactating females; 2. Cerebrovascular accident within one year; 3. Intracranial neoplasm or history of intracranial surgery; 4. History of bleeding diathesis; 5. Thrombocytopenia (platelet count of less than 100,000/µL); 6. Known International Normalized Ratio (INR) greater than 1.5 at screening; 7. Requirement for dialysis treatment (hemodialysis or peritoneal); 8. Estimated Glomeular filtration rate eGFR<30 ml/min; 9. Administration of abciximab within 24 hours of randomization or administration of eptifibatide or tirofiban within 12 hours of randomization; 10. Plans to continue oral anticoagulant, thienopyridine or GPIIb/IIIa antagonist therapy in the pre-operative period; 11. Known or suspected coagulopathy; 12. Refusal to receive blood transfusion; 13. Receipt of fibrinolytic therapy in the 12 hours preceding randomization; 14. Allergy, hypersensitivity, or contraindication to cangrelor, mannitol, sorbitol, or microcrystalline cellulose; 15. High likelihood of being unavailable for follow-up; 16. Participation in other studies involving the evaluation of other investigational drugs or devices within 30 days of randomization, 17. Any disease or condition which, in the judgment of the health care provider, would place the patient at undue risk by participating in the study.

Patients were randomized into two groups, a cangrelor plus standard of care (SOC) group, and a placebo plus SOC group. A dose study was performed, for cangrelor plus SOC and placebo plus SOC respectively. A dose of 0.75 µg/kg/min was confirmed for the cangrelor plus SOC and placebo plus SOC groups.

In the placebo plus SOC group, patients received only SOC, in which the thienopyridine is discontinued after the need for surgery had been determined and a placebo infusion is administered. In the cangrelor plus standard of care (SOC) group, a cangrelor infusion was started in addition to SOC when the thienopyridine was discontinued after the need for surgery had been determined. The infusions (cangrelor or matching placebo) were continued throughout the pre-operative period. Patients can wait 5 days after discontinuation of clopidogrel before undergoing surgery but the timing of surgery can vary and be left to the discretion of the health care practitioner with a maximum of 7 days of cangrelor infusion.

Daily measurements of platelet inhibition were taken using the VerifyNow® P2Y12 assay system.

All patients randomized receive SOC and waited up to five days after discontinuation of thienopyridine before undergoing CABG. Anti-platelet therapy with aspirin was maintained during this time. Anti-thrombotics such as unfractionated heparin and enoxaparin were allowed and given at the discretion of the health care provider. It was recommended that enoxaparin be discontinued >24 hours before CABG although concomitant use of other anti-platelet and anti-thrombic agents is contemplated by the invention described here. It was recognized that clinical events may occur leading to surgery before the 5 day waiting period is completed and therefore the decision to proceed to surgery was left to the discretion of the health care provider.

For patients randomized to the cangrelor arm, cangrelor infusion was started as quickly as possible and no more than 6 hours after randomization. Patients received an infusion of cangrelor, in addition to their SOC therapy, at a rate of 0.75 µg/kg/min.

Cangrelor was infused continuously via a dedicated peripheral or central line for at least about 2 days and up to about 7 days. The dose of cangrelor remained constant during the infusion period. The cangrelor infusion was terminated at least one and no more than six hours before induction of anesthesia for the scheduled CABG surgery. Induction of anesthesia is defined as the start time of IV anesthesia. Patients were infused with cangrelor for a minimum of 48 hours prior to termination.

Patients not randomized to receive cangrelor received a placebo infusion administered in the same manner as the cangrelor infusion in addition to their SOC therapy.

FIG. 4 includes a table that summarizes the study assessments by time point. This study consisted of 5 periods: Screening/Randomization Period, Pre-operative (Days 1-7 defined as the period from randomization to discontinuation of cangrelor), Intra-operative (from discontinuation of cangrelor to end of CABG surgery), Post-operative Follow-up (from end of CABG surgery to hospital discharge), and 30-Day Follow-up (30+5 days from time of CABG).

Pre-operative Period (Randomization until discontinuation of cangrelor). Just prior to the administration of cangrelor, a VerifyNow® P2Y$_{12}$ Assay was performed to obtain a baseline assessment. Testing was performed irrespective of the timing of last dose of thienopyridine received. Immediately following the VerifyNow® P2Y$_{12}$ Assay, the cangrelor composition was prepared and an infusion at the rate of 0.75 µg/kg/min was started. This infusion was maintained until 1 to 6 hours prior to anesthesia administration for the CABG surgery. The following tests were performed daily, at approximately the same time, during all days of cangrelor infusion: Hematology labs [hemoglobin, hematocrit, white blood cells (WBC), and platelet count] PRU and percent platelet inhibition determined by VerifyNow® P2Y$_{12}$ Assay Assessment of concomitant medications. Within 12 hours prior to surgery, the following procedures were conducted: Additional VerifyNow® P2Y$_{12}$ assay just prior to cangrelor termination. If the last on-infusion VerifyNow® sample was within 12 hours of cangrelor discontinuation, an additional draw was not required prior to termination of cangrelor.

Table 1 below represents the results of cangrelor and placebo treatment during the pre-operative period.

TABLE 1

Summary of PRU by Day

| | Stat | Cangrelor (N = 93) | Placebo (N = 90) |
|---|---|---|---|
| Screening | | | |
| Patients w/PRU <240 | n/N (%) | 53/85 (62.4) | 45/86 (52.3) |
| PRU: | N | 85 | 86 |
| | MEAN ± SD | 210.9 ± 94.0 | 214.1 ± 85.9 |
| | MEDIAN | 201.0 | 233.5 |
| | (Q1, Q3) | 166, 280 | 151, 279 |
| | (MIN, MAX) | 3, 418 | 10, 395 |
| Day 1 sample | | | |
| Patients w/PRU <240 | n/N (%) | 80/80 (100) | 34/76 (44.7) |
| PRU: | N | 80 | 76 |
| | MEAN ± SD | 45.5 ± 47.1 | 232.7 ± 74.2 |
| | MEDIAN | 31.0 | 249.0 |
| | (Q1, Q3) | 5, 78 | 178, 287 |
| | (MIN, MAX) | 0, 169 | 47, 367 |
| Day 2 sample | | | |
| Patients w/PRU <240 | n/N (%) | 69/70 (98.6) | 25/73 (34.2) |
| PRU: | N | 70 | 73 |
| | MEAN ± SD | 58.8 ± 58.1 | 239.2 ± 71.1 |
| | MEDIAN | 40.0 | 256.0 |
| | (Q1, Q3) | 6, 100 | 218, 282 |
| | (MIN, MAX) | 0, 271 | 64, 354 |
| Day 3 sample | | | |
| Patients w/PRU <240 | n/N (%) | 55/55 (100) | 21/57 (36.8) |
| PRU: | N | 55 | 57 |
| | MEAN ± SD | 69.2 ± 59.8 | 250.4 ± 64.7 |
| | MEDIAN | 52.0 | 263.0 |
| | (Q1, Q3) | 8, 117 | 200, 306 |
| | (MIN, MAX) | 0, 229 | 105, 358 |
| Day 4 sample | | | |
| Patients w/PRU <240 | n/N (%) | 33/33 (100) | 7/34 (20.6) |
| PRU: | N | 33 | 34 |
| | MEAN ± SD | 80.3 ± 61.7 | 286.5 ± 65.5 |
| | MEDIAN | 78.0 | 296.0 |
| | (Q1, Q3) | 33, 115 | 241, 344 |
| | (MIN, MAX) | 1, 219 | 118, 406 |
| Day 5 sample | | | |
| Patients w/PRU <240 | n/N (%) | 7/7 (100) | 6/24 (25.0) |
| PRU: | N | 7 | 24 |
| | MEAN ± SD | 52.1 ± 58.1 | 284.0 ± 64.0 |
| | MEDIAN | 30.0 | 285.5 |
| | (Q1, Q3) | 9, 117 | 244, 328 |
| | (MIN, MAX) | 7, 151 | 140, 388 |
| Day 6 sample | | | |
| Patients w/PRU <240 | n/N (%) | 6/6 (100) | 3/14 (21.4) |
| PRU: | N | 6 | 14 |
| | MEAN ± SD | 62.7 ± 74.7 | 291.3 ± 54.1 |
| | MEDIAN | 45.5 | 280.0 |
| | (Q1, Q3) | 9, 67 | 250, 329 |
| | (MIN, MAX) | 3, 206 | 217, 399 |
| Day 7 sample | | | |
| Patients w/PRU <240 | n/N (%) | 1/1 (100) | 0/2 (0.0) |
| PRU: | N | 1 | 2 |
| | MEAN ± SD | 3.0 ± . | 343.5 ± 4.9 |
| | MEDIAN | 3.0 | 343.5 |
| | (Q1, Q3) | 3, 3 | 340, 347 |
| | (MIN, MAX) | 3, 3 | 340, 347 |
| Last on-treatment sample | | | |
| Patients w/PRU <240 | n/N (%) | 83/84 (98.8) | 26/84 (31.0) |
| PRU: | N | 84 | 84 |
| | MEAN ± SD | 68.9 ± 67.8 | 263.7 ± 68.3 |
| | MEDIAN | 53.0 | 263.5 |
| | (Q1, Q3) | 8, 110 | 227, 311 |
| | (MIN, MAX) | 0, 271 | 81, 399 |

TABLE 1-continued

Summary of PRU by Day

|  | Stat | Cangrelor (N = 93) | Placebo (N = 90) |
|---|---|---|---|
| Last post-treatment pre-CABG | | | |
| Patients w/PRU <240 | n/N (%) | 21/78 (26.9) | 15/75 (20.0) |
| PRU: | N | 78 | 75 |
| | MEAN ± SD | 279.7 ± 106.5 | 297.8 ± 67.3 |
| | MEDIAN | 293.0 | 299.0 |
| | (Q1, Q3) | 228, 357 | 256, 345 |
| | (MIN, MAX) | 1, 471 | 144, 445 |

The data in Table 1 indicates that infusion of Cangrelor at a dose of 0.75 μg/kg/min between day 1 to day 7 maintains PRU values below 240 in over 90% of the patients studied. The table further indicates that for the "last post-treatment pre-CABG" where cangrelor infusion is terminated but prior to CABG, the level of PRU has resumed to levels prior to cangrelor treatment.

Intra-operative Period (Period from discontinuation of cangrelor until end of CABG surgery) The Intra-operative period started at termination of cangrelor infusion (surgery start is defined as time of first incision). Cangrelor infusion was stopped at least 1 hour and a maximum of 6 hours prior to administration of anesthesia for surgery. Standard of care treatment was used for the surgical period. Collection of the following assessments were conducted during this period: Serum creatinine and LFTs—following discontinuation of cangrelor but prior to surgery (surgery start time is defined as the time of first surgical incision). VerifyNow® P2Y12 assay just prior to first surgical incision. Concomitant medications and assessments of adverse events, serious adverse events and clinical endpoints.

In the case of administering and ceasing the therapy prior to surgery in accordance with one embodiment of the present invention, such use allows patients to undergo surgery or other invasive procedures without excessive perioperative bleeding.

Table 2 represents the bleeding risks associated with cangrelor and placebo treatment.

TABLE 2

Summary of CABG Related Bleeding during the CABG Procedure through Hospital Discharge

|  | Stat | Cangrelor (N = 105) | Placebo (N = 102) |
|---|---|---|---|
| CABG related bleeding | n/N (%) | 10/102 (9.8) | 10/96 (10.4) |
| Fatal bleeding | n/N (%) | 0 | 0 |
| Periop. intracranial bleeding | n/N (%) | 0 | 0 |
| Re operation for bleeding | n/N (%) | 2/102 (2.0) | 2/96 (2.1) |
| Whole Blood or pRBC Transfusion >= 5 units | n/N (%) | 7/102 (6.9) | 8/96 (8.3) |
| 24 hour CT output >= 2 L | n/N (%) | 3/102 (2.9) | 4/96 (4.2) |

The results of Table 2 indicates that bleeding risk associated with cangrelor treatment is the same as or similar to treatment with placebo.

Table 3 represents the overall incidence of ischemic events

TABLE 3

Overall Incidence of Ischemic Events

|  | Stat | Cangrelor (N = 106) | Placebo (N = 101) |
|---|---|---|---|
| Pre-procedure | | | |
| Death/MI/IDR/Stroke | n/N (%) | 6/106 (5.7) | 4/101 (4.0) |
| Death | n/N (%) | 1/106 (0.9) | 3/101 (3.0) |
| MI | n/N (%) | 2/106 (1.9) | 0/101 (0.0) |
| IDR | n/N (%) | 4/106 (3.8) | 0/101 (0.0) |
| Stroke | n/N (%) | 0/106 (0.0) | 1/101 (1.0) |
| Post-procedure | | | |
| Death/MI/IDR/Stroke | n/N (%) | 4/102 (3.9) | 4/96 (4.2) |
| Death | n/N (%) | 1/102 (1.0) | 2/96 (2.1) |
| MI | n/N (%) | 2/102 (2.0) | 1/96 (1.0) |
| IDR | n/N (%) | 2/102 (2.0) | 0/96 (0.0) |
| Stroke | n/N (%) | 1/102 (1.0) | 1/96 (1.0) |
| Pre and Post-procedures | | | |
| Death/MI/IDR/Stroke | n/N (%) | 10/106 (9.4) | 8/101 (7.9) |
| Death | n/N (%) | 2/106 (1.9) | 5/101 (5.0) |
| MI | n/N (%) | 4/106 (3.8) | 1/101 (1.0) |
| IDR | n/N (%) | 6/106 (5.7) | 0/101 (0.0) |
| Stroke | n/N (%) | 1/106 (0.9) | 2/101 (2.0) |

The results of Table 3 indicates that the ischemic events relating to the methods described herein with the use of cangrelor is comparable to the placebo.

Post-operative Period (Period from end of CABG surgery to hospital discharge) The following procedures were performed following surgery (end of CABG surgery is defined as the placement of the last suture): VerifyNow® P2Y12 Assay was performed within 1 hour following surgery Hematology labs, 12 lead-ECG and VerifyNow™ P2Y12 Assay were performed 24-hours (±1 h) following surgery. Chest tube output will be assessed at 4 hours (±1 h) and 24 hours (±1 h) following surgery.

Example 3

In another example and in accordance with one embodiment of the present invention, the administration of the at least one reversible, short-acting P2Y12 inhibitor occurs during an invasive procedure being performed on the subject. In this manner, it is contemplated that the administration of the inhibitor would occur intravenously as the subject cannot take the therapy orally.

Example 4a

In another example and in accordance with another embodiment of the present invention, the administration of the at least one reversible, short-acting P2Y12 inhibitor occurs after an invasive procedure has been performed on the subject. The administration of the inhibitor in the post surgery scenario can occur in a variety of methods as described above. It is contemplated that the administration of the inhibitor may also occur intravenously post surgery if the subject cannot take the therapy orally, for example, if the subject is comatose.

Example 4b

The Study for Using Cangrelor in Early Post-Operative Period

Current standard of care for anti-platelet maintenance therapy after PCI in patients with implanted stents is based on recommendations of the American College of Cardiology/American Heart Association (ACC/AHA) guidelines (Fleisher L A, et al., ACC/AHA 2007 guidelines on perioperative cardiovascular evaluation and care for noncardiac surgery: a report of the ACC/AHA Task Force on Practice Guidelines. Circulation. 2007 Oct. 23; 116(17):e418-99) that suggest an early initiation of dual anti-platelet therapy and continuation of maintenance therapy with aspirin and clopidogrel after PCI from 6 to 12 months, depending on the stent type, in order to prevent post-procedural stent thrombosis. Both aspirin and clopidogrel are irreversible platelet antagonists, therefore ACC/AHA guidelines recommend cessation of clopidogrel before non-emergent surgical procedures in order to minimize bleeding risks.

However, should patients with implanted stents require a surgical procedure, early cessation of clopidogrel would increase the risk for ischemic events and stent thrombosis due to a "rebound" effect of platelet activation (Berger et al., *Circulation*. 2002 Oct. 22; 106(17):2284-7; Ho et al. *JAMA*. 2008 Feb. 6; 299(5):532-9). Conversely, maintaining irreversible platelet inhibition with aspirin and clopidogrel leads to unacceptable operative bleeding risk (Fox et al., *Circulation*. 2004; 110; 1202-1208; Shim et al., *J Thorac Cardiovasc Surg*. 2007 July; 134(1):59-64; Pickard et al., *Pharmacotherapy*. 2008 March; 28(3):376-92. Review).

Because of the risk of bleeding from the surgical sites, surgeons prefer to avoid using anticoagulant agents in early post-operative period especially with irreversible oral therapy that will not allow predicting the level of platelet inhibition and fast recovery of platelet function when surgical procedure could be associated with high risk of post-operative bleeding.

It is well known that surgical interventions trigger platelet activation and aggregation, hence increasing the risk of stent thrombosis in post-operative period if patient do not continue anti-platelet therapy.

It has been demonstrated in several studies that early initiation of anticoagulant therapy may diminish the risk of venous thrombosis (Segers A. *J Thromb Haemost*. 2008 August; 6(8):1313-8; Turpie et al., *Lancet*. 2009 May 1), however there is no consensus or standard antiplatelet therapy regimen designed to reduce the risk of arterial stent thrombosis in patients with implanted stents requiring surgical procedures.

Typically, at conclusion of surgical procedure a complete hemostasis is achieved, however, the risk of bleeding from the surgical site remains high during the first post-operative hours. Initiation of anti-platelet therapy during the immediate-early period after surgery may further increase that risk. Conversely, a delay of continuation of anti-platelet maintenance therapy will significantly increase the risk of stent thrombosis, considering that surgical procedure triggers platelet activation and aggregation. Therefore, an early therapy with reversible anti-platelet agent that could be titrated to a desirable level of platelet inhibition and have ultra-short platelet function recovery time could be beneficial in preventing stent thrombosis in that category of patients. Moreover, this type of agent will be safe because it may allow complete recovery of platelet function after discontinuation in case of bleeding.

Cangrelor is a potent, reversible and specific $P2Y_{12}$ receptor antagonist that would allow overcoming the limitations of currently used dual anti-platelet therapy with aspirin and clopidogrel thanks to its rapid onset and offset of action with steady-state plasma concentrations that can be achieved within minutes and titrated to modulate the level of platelet inhibition and most importantly, it is rapidly metabolized with an short half-life, allowing complete recovery of platelet function in less than 60 min. Therefore, cangrelor could be an ideal anti-platelet agent for managing platelet inhibition in early post-operative period in patients with implanted stents requiring a surgical procedure.

The optimal platelet inhibitory dose and regimen for cangrelor infusion in post-operative period and transitioning to oral anti-platelet therapy can be determined.

The patient population can be ACS patients with implanted stents after PCI who require a major surgical procedure (CABG, GI anastomoses, pulmonary resection, prostatectomy, orthopedic procedures, etc.), N=40 subjects (4 groups with 10 subjects in each group). Cangrelor infusion will be initiated 1-2 hours after completion of surgical procedure at surgeons' discretion. The subjects will be randomized into the following groups:

Group 1: Cangrelor 0.5 μg/kg/min dose infusion for 24 hrs transitioning to oral antiplatelet therapy with 300 mg of clopidogrel loading dose after infusion discontinuation followed by 75 mg daily maintenance dose thereafter Group 2: Cangrelor 0.5 μg/kg/min infusion for 24 hrs transitioning to oral antiplatelet therapy with 600 mg of clopidogrel loading dose after infusion discontinuation followed by 75 mg daily maintenance dose thereafter Group 3: Cangrelor 1 μg/kg/min infusion for 24 hrs transitioning to oral antiplatelet therapy after infusion discontinuation transitioning to oral antiplatelet therapy with 300 mg of clopidogrel loading dose after infusion discontinuation followed by 75 mg daily maintenance dose thereafter Group 4: Cangrelor 1 μg/kg/min infusion for 24 hrs transitioning to oral antiplatelet therapy after infusion discontinuation transitioning to oral antiplatelet therapy with 600 mg of clopidogrel loading dose after infusion discontinuation followed by 75 mg daily maintenance dose thereafter The primary endpoints will be: (1) acute sent thrombosis during the 48 hrs after the surgical procedure, and (2) major and minor bleedings during the 48 hrs after the surgical procedure.

The methods of evaluation will be: (1) platelet aggregation using VerifyNow-P2Y12 test, (2) hemodynamic measurements, (3) blood tests, (4) clinical observations for minor capillary bleeding signs (petechia, hematoma), (5) Diagnostic imaging of intracranial, peritoneal and pleural cavities using CT, MRI, US, when necessary to detect potential bleeding complications (blood accumulation).

TABLE 4

| Study Assessment | Screening/ Randomization Pretreatment/ Screening Period [1] | Pre-operative | | | Intra-operative During surgery[2] | Post-Operative through Discharge | | | | FUP 30-d FUP (+ 5 d) |
| --- | --- | --- | --- | --- | --- | --- | --- | --- | --- | --- |
| | | Randomization | Days 1-7 | Pre-surgery | | Immediately Post Surgery | 4 h (± 1 h) post surgery | 24-h (± 1 hr) post surgery | Discharge | |
| Informed consent | X | | | | | | | | | |
| Medical History | X | | | | | | | | | |
| Review of inclusion/exclusion criteria | X | | | | | | | | | |
| Pregnancy test (serum or urine), if applicable | X | | | | | | | | | |
| PT/INR | X | | | | | | | | | |
| Previous medications | X | | | | | | | | | |
| Hematology (Hgb, Hct, WBC, platelets) | X | | X[4] | | | | | X | | |
| Serum creatinine and LFTs | X | | | | X[5] | | | | | |
| 12-lead ECG | X | | | | | | | X | | |
| CK, CK-MB | X | | | | | | | | | |
| IVRS randomization | | X[11] | | | | | | | | |
| VerifyNow ™ P2Y$_{12}$ Assay | | X[6] | X[7] | X[8] | X[9] | X | | X | | |
| Study Drug Administration | | X | X | X[10] | | | | | | |
| Concomitant Medications | | | | | | X | | | | |
| Clinical Endpoint Assessments | | | | | | | X | | | |
| Adverse Event Reporting | | | | | | X | | | | |
| SAE Reporting | | | | | | X | | | | |

[1] Screening Period tests are to be conducted within 24 hours prior to randomization.
[2] Surgery start is defind as time of first incision; surgery stop is defind as last suture placed
[3] Immediately is defind as within 1 hour post end of CABG surgery unless otherwise defined
[4] Hematology tests are to be drawn daily during the infusion period, at approximately the same time each day
[5] Pre-surgery serum creatinine and LFTs should be drawn following the discontinuation of study drug infusion, but prior to CABG surgery
[6] VerifyNow ™ P2Y$_{12}$ Assay sample to be drawn just prior to initiation of study drug
[7] VerifyNow ™ P2Y$_{12}$ Assay samples are to be taken daily during the infusion period should be at approximately the same time each day, in conjunction with daily labs if possible
[8] Pre-surgery VerifyNow ™ P2Y$_{12}$ Assay testing should be done prior to discontinuation of study drug infusion. Patients must have a minimum of 48 hours on cangrelor infusion prior to termination. If the last on-infusion VerifyNow sample was within 12 hours of study drug discontinuation, an additional draw is not required prior to termination of cangrelor
[9] VerifyNow ™ P2Y$_{12}$ Assay sample to be drawn just prior to surgical incision.
[10] Study drug infusion should he stopped at no less than 1 and no more than 6 hours prior to anesthesia for surgery.
[11] IVRS randomization not appliable to Stage I. Patients will be enrolled via a manual process.

Table 4 shows the studied assessments by time point.

Those of ordinary skill in the art will recognize that many modifications and variations of the present invention may be implemented without departing from the spirit or scope of the invention. Thus, it is intended that the present invention cover the modification and variations of this invention provided they come within the scope of the appended claims and their equivalents.

The invention claimed is:

1. A method of maintaining or reducing platelet activity in a patient in need thereof comprising:
administering to the patient a therapeutically effective amount of cangrelor wherein the patient was previously treated with a long-acting irreversible platelet inhibitor, prior to the patient undergoing an invasive procedure.

2. The method of claim 1 wherein administration of cangrelor is at a range of between about 0.1 ug/kg/min to about 5 ug/kg/min.

3. The method of claim 1 wherein administration of cangrelor is at a range of between about 0.5 ug/kg/min to about 2 ug/kg/min.

4. The method of claim 1 wherein administration of cangrelor is at a range of between about 0.5 ug/kg/min to about 1 ug/kg/min.

5. The method of claim 1 wherein administration of cangrelor is about 0.75 ug/kg/min.

6. The method of claim 1 wherein the long-acting irreversible platelet inhibitor is a thienopyridine.

7. The method of claim 6 wherein the thienopyridine is selected from the group consisting of clopidogrel, ticlopindine, and prasugrel.

8. The method of claim 1 wherein administration of cangrelor is started within about 3 days of ceasing administration of the long-acting irreversible platelet inhibitor.

9. The method of claim 1 wherein cangrelor is continuously administered between about 2 days to about 7 days.

10. The method of claim 1 wherein administration of cangrelor is discontinued and allowing platelet activity to return to pre-cangrelor administration levels wherein the measured P2Y$_{12}$ reaction unit (PRU) level is greater than 240, prior to the patient undergoing an invasive procedure.

11. The method of claim 1 wherein administration of cangrelor is in an amount to maintain the measured P2Y$_{12}$ reaction unit (PRU) value at less than 240.

12. The method of claim 1 wherein cangrelor is concurrently administered with a second therapeutic agent, wherein the second therapeutic agent comprises one or more of the group consisting of aspirin, bivalirudin, heparin, fondaprinux sodium, warfarin, coumarin, streptokinase, alteplase, reteplase, urokinase, tenecteplase, eptifibatide, abciximab, tirofiban, epsilon amino-caproic acid, and tranexamic acid.

13. The method of claim 12 wherein said second therapuetic agent is streptokinase, alteplase, reteplase, urokinase, tenecteplase, aspirin, bivalirudin, heparin, warfarin, eptifibatide, abciximab or tirofiban.

14. The method of claim 1 wherein the risk of bleeding is not increased.

15. A method for maintaining or reducing platelet activity in a patient comprising: administering to the patient a therapeutically effective amount of cangrelor prior to the patient undergoing an invasive procedure wherein oral administration of platelet inhibition therapy is contra-indicated.

16. The method of claim 15 wherein administration of cangrelor is at a range of between about 0.1 ug/kg/min to about 5 ug/kg/min.

17. The method of claim 15 wherein administration of cangrelor is at a range of between about 0.5 ug/kg/min to about 2 ug/kg/min.

18. The method of claim 15 wherein administration of cangrelor is about 0.75 ug/kg/min.

19. The method of claim 15 wherein cangrelor is continuously administered between about 2 days to about 7 days.

20. The method of claim 15 wherein administration of cangrelor is discontinued and allowing platelet activity to return to pre-cangrelor administration levels wherein the measured $P2Y_{12}$ reaction unit (PRU) level is greater than 240, prior to the patient undergoing an invasive procedure.

21. The method of claim 15 wherein administration of cangrelor is by continuous infusion.

22. The method of claim 15 wherein the administration of cangrelor is by a bolus and continuous infusion.

23. A method of maintaining or reducing platelet activity in a patient in need thereof comprising:
administering to a patient in need thereof an effective amount of cangrelor prior to undergoing a invasive procedure wherein the measured $P2Y_{12}$ reaction unit (PRU) is maintained at or below about 240 during administration of cangrelor.

24. The method of claim 23 wherein the measured PRU is maintained at a range of about 30 to about 240 during administration of cangrelor.

25. The method of claim 23 wherein administration of cangrelor is at a range of between about 0.5 ug/kg/min to about 2 ug/kg/min.

26. The method of claim 23 wherein administration of cangrelor is about 0.75 ug/kg/min.

27. The method of claim 23 wherein administration of cangrelor is started within about 3 days of ceasing administration of the long-acting irreversible platelet inhibitor.

28. The method of claim 23 wherein cangrelor is continuously administered between about 2 days to about 7 days.

29. The method of claim 23 wherein administration of cangrelor is discontinued and allowing platelet activity to return to pre-cangrelor administration levels wherein the measured PRU level is greater than 240, prior to the patient undergoing an invasive procedure.

30. A method of maintaining or reducing platelet activity comprising:
administering to a patient in need thereof an effective amount of cangrelor wherein the patient was previously treated with a thienopyridine prior to undergoing an invasive procedure wherein at least about 60% of the platelet activity is inhibited.

31. The method of claim 30 wherein administration of cangrelor is at a range of between about 0.1 ug/kg/min to about 5 ug/kg/min.

32. The method of claim 30 wherein administration of cangrelor is about 0.75 ug/kg/min.

33. The method of claim 30 wherein administration of cangrelor is within about 3 days of ceasing administration of the long-acting irreversible platelet inhibitor.

34. The method of claim 30 wherein cangrelor is continuously administered between about 2 days to about 7 days.

35. The method of claim 30 wherein administration of cangrelor is discontinued and allowing platelet activity to return to pre-cangrelor administration levels wherein the measured $P2Y_{12}$ reaction unit (PRU) level is greater than 240, prior to the patient undergoing an invasive procedure.

36. A method of maintaining or reducing platelet activity prior to undergoing an invasive procedure, comprising:
administering a therapeutically effective amount of cangrelor to a patient in need thereof wherein the $P2Y_{12}$ reaction unit (PRU) level is at or below 240, ceasing administration of cangrelor wherein the PRU levels is similar to pre cangrelor administration levels, prior to said patient undergoing an invasive procedure.

37. The method of claim 36 wherein administration of cangrelor is at a range of between about 0.1 ug/kg/min to about 5 ug/kg/min.

38. The method of claim 36 wherein administration of cangrelor is about 0.75 ug/kg/min.

39. The method of claim 36 wherein cangrelor is continuously administered between about 2 days to about 7 days.

40. The method of treating or preventing thrombosis comprising:
administering a therapeutically effective amount of cangrelor to a patient in need thereof where said patient was previously treated with a long-acting irreversible platelet inhibitor, wherein the risk of bleeding is not increased.

41. The method of claim 40 wherein administration of cangrelor is at a range of between about 0.1 ug/kg/min to about 5 ug/kg/min.

42. The method of claim 40 wherein administration of cangrelor is at a range of between about 0.5 ug/kg/min to about 1 ug/kg/min.

43. The method of claim 40 wherein administration of cangrelor is within about 3 days of ceasing administration of the long-acting irreversible platelet inhibitor.

44. The method of claim 40 wherein cangrelor is continuously administered between about 2 days to about 7 days.

45. The method of claim 40 wherein the measured $P2Y_{12}$ reaction unit (PRU) is maintained below 240 during the administration of cangrelor.

46. A method of reducing platelet activity in a patient in need thereof comprising:
administering during the perioperative period to a patient in need of an invasive procedure a therapeutically effective amount of cangrelor wherein the measured $P2Y_{12}$ reaction unit (PRU) is below 240.

47. The method of claim 46 wherein cangrelor is continuously administered between about 2 days to about 7 days.

* * * * *